(12) United States Patent
Swanson et al.

(10) Patent No.: US 11,543,396 B2
(45) Date of Patent: Jan. 3, 2023

(54) GAS SENSOR WITH SEPARATE CONTAMINANT DETECTION ELEMENT

(71) Applicant: MSA TECHNOLOGY, LLC, Cranberry Township, PA (US)

(72) Inventors: Meghan E. Swanson, Pittsburgh, PA (US); Daniel D. Santoro, Jr., Pittsburgh, PA (US); Michael Alvin Brown, Cranberry Township, PA (US); Mark Flori Zanella, Sr., Chicora, PA (US); Christopher S. Detka, Pittsburgh, PA (US)

(73) Assignee: MSA Technology, LLC, Cranberry Township, PA (US)

( * ) Notice: Subject to any disclaimer, the term of this patent is extended or adjusted under 35 U.S.C. 154(b) by 718 days.

(21) Appl. No.: 16/437,487

(22) Filed: Jun. 11, 2019

(65) Prior Publication Data

US 2020/0393432 A1   Dec. 17, 2020

(51) Int. Cl.
*G01N 33/00* (2006.01)
*G01N 27/16* (2006.01)
*G01N 27/404* (2006.01)

(52) U.S. Cl.
CPC ......... *G01N 33/0031* (2013.01); *G01N 27/16* (2013.01); *G01N 27/404* (2013.01);
(Continued)

(58) Field of Classification Search
CPC .. G01N 27/16; G01N 33/0047; G01N 33/005; G01N 33/0052; G01N 33/0044;
(Continued)

(56) References Cited

U.S. PATENT DOCUMENTS

| 4,533,520 A | 8/1985 | Bossart |
|---|---|---|
| 4,627,269 A | 12/1986 | Forster |

(Continued)

FOREIGN PATENT DOCUMENTS

| CN | 107533023 A | * 1/2018 | ............ G01N 25/32 |
|---|---|---|---|
| EP | 0500598 B1 | 3/1997 | |

(Continued)

OTHER PUBLICATIONS

GasAlertMicro 5 O2, Co, H2S, PH3, SO2, Cl2, NH3, NO2, HCN, ClO2, O3, VOC, and Combustibles—1,2, 3, 4, and 5 Gas Detectors. (Year: 2006).*

(Continued)

*Primary Examiner* — David A. Rogers
(74) *Attorney, Agent, or Firm* — Bartony & Associates LLC

(57) ABSTRACT

A system for detecting an analyte gas in an environment includes a first gas sensor, a first contaminant sensor separate and spaced from the first gas sensor, and electronic circuitry in electrical connection with the first gas sensor to determine if the analyte gas is present based on a response of the first gas sensor. The electronic circuitry is further in electrical connection with the first contaminant sensor to measure a response of the first contaminant sensor over time. The measured response of the first contaminant sensor varies with an amount of one or more contaminants to which the system has been exposed in the environment over time.

21 Claims, 10 Drawing Sheets

(52) U.S. Cl.
CPC ..... *G01N 33/0006* (2013.01); *G01N 33/0013* (2013.01); *G01N 33/0016* (2013.01); *G01N 33/0075* (2013.01)

(58) Field of Classification Search
CPC ............ G01N 33/0042; G01N 33/004; G01N 33/0039; G01N 33/0037
See application file for complete search history.

(56) References Cited

U.S. PATENT DOCUMENTS

| | | | |
|---|---|---|---|
| 4,720,421 A * | 1/1988 | Khilnani | G01N 27/16 428/222 |
| 4,854,155 A * | 8/1989 | Poli | G01N 27/16 73/31.05 |
| 5,061,447 A * | 10/1991 | Ono | G01N 27/16 324/706 |
| 5,401,470 A | 3/1995 | Poli | |
| 5,427,672 A * | 6/1995 | Bocker | G01N 27/4075 204/429 |
| 5,528,225 A | 6/1996 | Sakai | |
| 5,599,584 A | 2/1997 | Champney, Jr. | |
| 5,685,895 A * | 11/1997 | Hagiwara | B01D 53/30 96/117 |
| 5,780,715 A | 7/1998 | Imblum | |
| 5,813,764 A * | 9/1998 | Visser | G01N 25/30 73/25.05 |
| 5,902,556 A * | 5/1999 | Van De Vyver | G01N 27/122 422/174 |
| 6,131,438 A | 10/2000 | Zanini-Fisher | |
| 6,705,152 B2 | 3/2004 | Routkevitch | |
| 6,756,016 B2 | 6/2004 | Miller | |
| 7,007,542 B2 * | 3/2006 | Wang | G01N 27/16 73/23.21 |
| 7,041,256 B2 | 5/2006 | Wang | |
| 7,566,848 B2 * | 7/2009 | Takahashi | G01N 33/005 219/202 |
| 7,622,080 B2 * | 11/2009 | Enquist | G01N 33/005 422/50 |
| 7,875,244 B2 * | 1/2011 | Schlichte | G01N 27/16 436/139 |
| 8,425,846 B2 * | 4/2013 | Takahashi | G01N 27/16 422/98 |
| 8,826,721 B2 | 9/2014 | Zanella, Sr. | |
| 9,228,967 B2 | 1/2016 | Alepee | |
| 10,234,412 B2 * | 3/2019 | Swanson | G01N 27/16 |
| 10,495,620 B2 * | 12/2019 | Johansen | G01N 33/0006 |
| 10,533,965 B2 * | 1/2020 | Wang | G01N 27/4075 |
| 10,578,573 B2 * | 3/2020 | Zanella, Sr. | G01N 27/16 |
| 10,627,379 B2 * | 4/2020 | Zanella, Sr. | G01N 27/16 |
| 10,705,041 B2 * | 7/2020 | Swanson | G01N 27/407 |
| 10,942,157 B2 * | 3/2021 | Brahem | G01N 33/0047 |
| 10,948,469 B2 * | 3/2021 | Zanella, Sr. | G01N 33/007 |
| 2002/0146352 A1 | 10/2002 | Wang | |
| 2003/0039299 A1 | 2/2003 | Horovitz | |
| 2005/0220672 A1 * | 10/2005 | Takahashi | G01N 27/16 422/94 |
| 2006/0019402 A1 | 1/2006 | Wang | |
| 2006/0249384 A1 | 11/2006 | Kim | |
| 2008/0034841 A1 | 2/2008 | Bahs | |
| 2009/0016934 A1 * | 1/2009 | Schlichte | G01N 27/16 422/94 |
| 2011/0100090 A1 | 5/2011 | Zanella, Sr. | |
| 2011/0110019 A1 | 5/2011 | Varade | |
| 2012/0318037 A1 | 12/2012 | Lee | |
| 2014/0273263 A1 | 9/2014 | Zanella, Sr. | |
| 2017/0024992 A1 | 1/2017 | Chey | |
| 2018/0128763 A1 | 5/2018 | Swanson | |
| 2018/0335411 A1 | 11/2018 | Zanella, Sr. | |
| 2018/0335412 A1 | 11/2018 | Zanella, Sr. | |
| 2018/0353885 A1 | 12/2018 | Swanson | |
| 2020/0025701 A1 | 1/2020 | Brown | |
| 2020/0028386 A1 | 1/2020 | Sexton | |
| 2021/0255131 A1 * | 8/2021 | Evju | G01N 33/005 |

FOREIGN PATENT DOCUMENTS

| | | |
|---|---|---|
| GB | 1550615 | 8/1979 |
| JP | 2000039413 | 2/2000 |
| JP | 2007048578 | 2/2007 |
| JP | 2008241554 A * | 10/2008 |
| JP | 2010054230 | 3/2010 |
| JP | 2012013603 A * | 1/2012 |
| JP | 2012247239 | 12/2012 |
| JP | 2013509594 | 3/2013 |
| WO | WO2008157391 A1 | 12/2008 |
| WO | 2018085026 | 5/2018 |
| WO | 2018212965 | 11/2018 |
| WO | 2018212966 | 11/2018 |
| WO | WO2020018526 A1 | 1/2020 |
| WO | WO2020023425 A1 | 1/2020 |
| WO | WO2020251925 | 12/2020 |
| WO | WO2020251931 | 12/2020 |

OTHER PUBLICATIONS

Mosely, P.T. and Tofield, B.C., ed., Solid State Gas Sensors, Adams Hilger Press, Bristol, England (1987).
Firth, J.G. et al., Combustion and Flame 21, 303 (1973).
Cullis, C.F., and Firth, J.G., Eds., Detection and Measurement of Hazardous Gases, Heinemann, Exeter, 29 (1981).
V. Palmisano et al. Selectivity and resistance to poisons of commercial hydrogen sensors, International Journal of Hydrogen Energy, vol. 40, No. 35, (Sep. 1, 2015), pp. 11740-11747.
Ruffer, Daniel et al., New Digital Metal-Oxide (MOx) Sensor Platform, Sensors, vol. 18, No. 4, (Mar. 31, 2018), pp. 1-12.
Schuler, M. et al., A novel approach for detecting HMDSO poisoning of metal oxide gas sensors and improving their stability by temperature cycled operation, Journal of Sensors and Sensor Systems, vol. 4, No. 2, (Oct. 19, 2015), pp. 305-311.

* cited by examiner

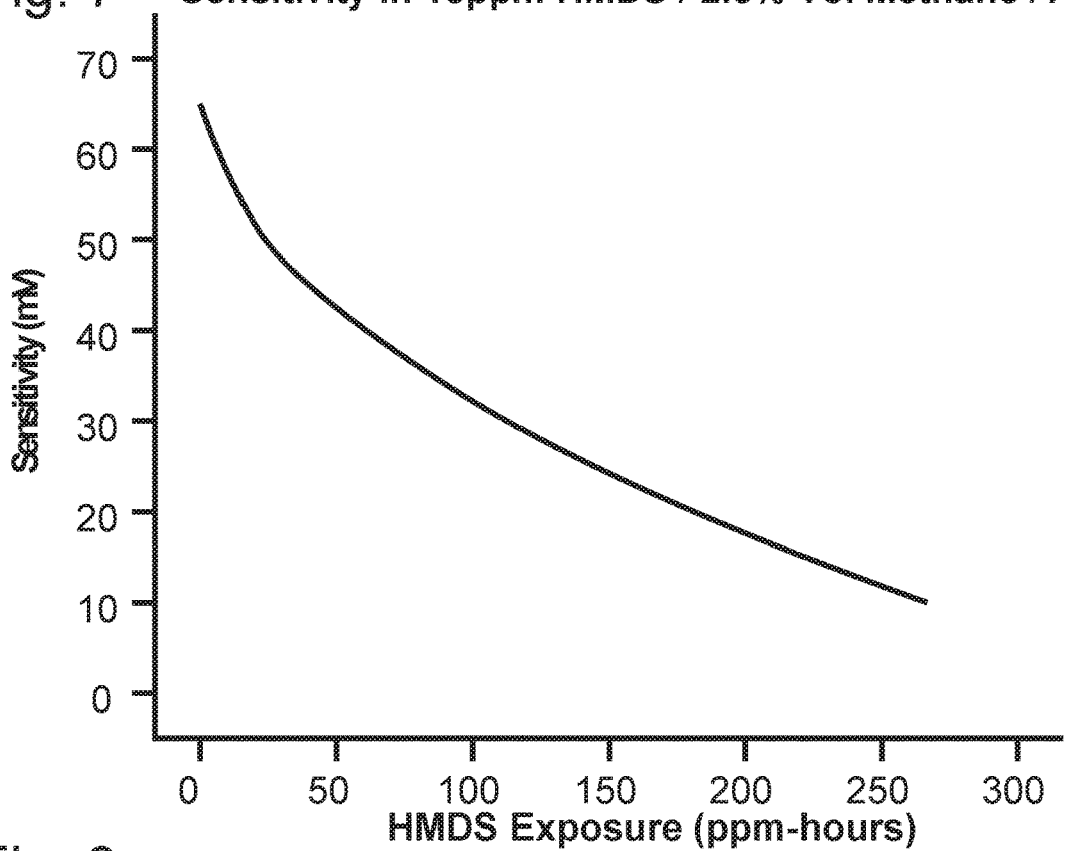
Fig. 7 Sensitivity in 15ppm HMDS / 2.5% Vol Methane / Air
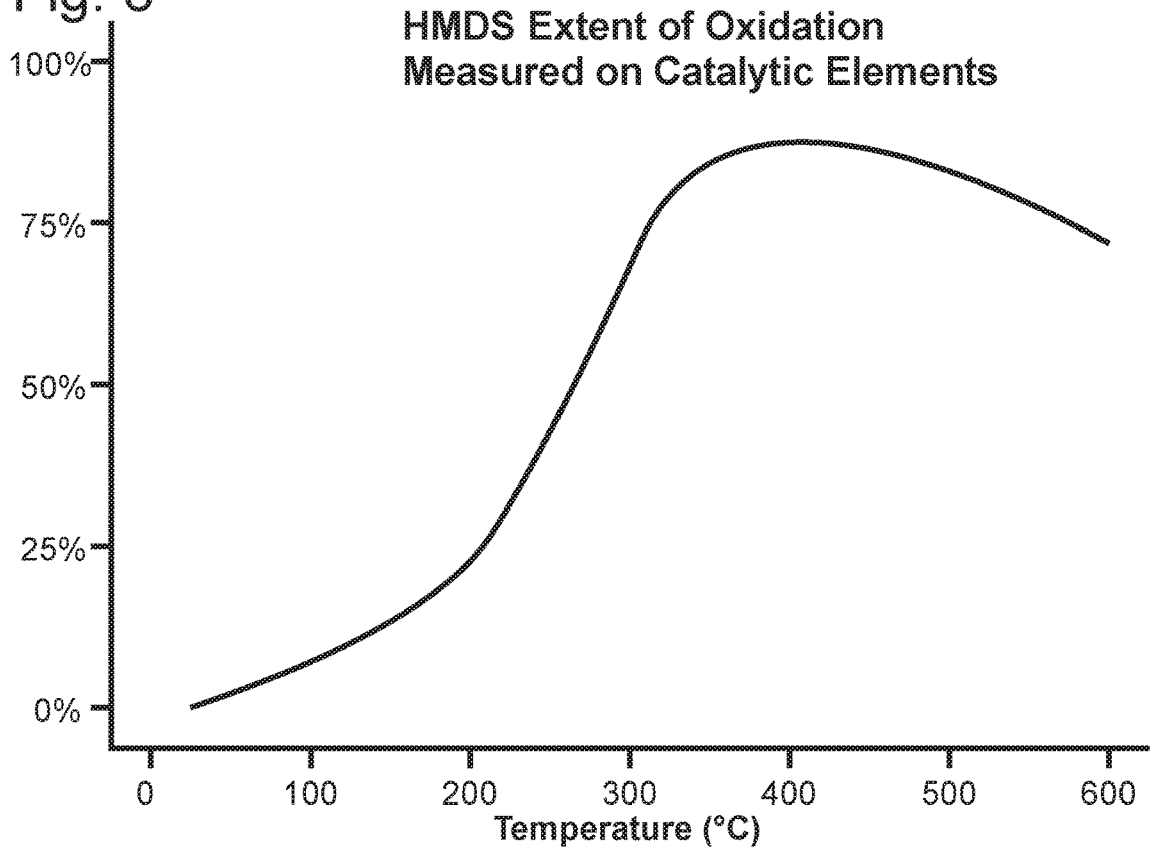
Fig. 8 HMDS Extent of Oxidation Measured on Catalytic Elements

GAS SENSOR WITH SEPARATE CONTAMINANT DETECTION ELEMENT

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Catalytic or combustible (flammable) gas sensors have been in use for many years to, for example, prevent accidents caused by the explosion of combustible or flammable gases. In general, combustible gas sensors operate by catalytic oxidation of combustible gases.

The operation of a catalytic combustible gas sensor proceeds through electrical detection of the heat of reaction of a combustible gas on the oxidation catalyst, usually through a resistance change. The oxidation catalysts typically operate in a temperature above 300° C. to catalyze combustion of an analyte (for example, in the range of 350 to 600° C. temperature range for methane detection). Therefore, the sensor must sufficiently heat the sensing element through resistive heating. In a number of combustible gas sensors, the heating and detecting element are one and the same and composed of a platinum alloy because of its large temperature coefficient of resistance and associated large signal in target/analyte gas. The heating element may, for example, be a helical coil of fine wire or a planar meander formed into a hotplate or other similar physical form. The catalyst being heated often is an active metal catalyst dispersed upon a refractory catalyst substrate or support structure. Usually, the active metal is one or more noble metals such as palladium, platinum, rhodium, silver, and the like and the support structure is a refractory metal oxide including, for example, one or more oxides of aluminum, zirconium, titanium, silicon, cerium, tin, lanthanum and the like. The support structure may or may not have high surface area (for example, greater than or equal to 75 $m^2/g$). Precursors for the support structure and the catalytic metal may, for example, be adhered to the heating element in one step or separate steps using, for example, thick film or ceramic slurry techniques. A catalytic metal salt precursor may, for example, be heated to decompose it to the desired dispersed active metal, metal alloy, and/or metal oxide.

As illustrated in FIGS. 1A and 1B, a number of conventional combustible gas sensors such as illustrated sensor 10 typically include an element such as a platinum heating element wire or coil 20 encased in a refractory (for example, alumina) bead 30, which is impregnated with a catalyst (for example, palladium or platinum) to form an active or sensing element, which is sometimes referred to as a pelement 40, pellistor, detector or sensing element. A detailed discussion of pelements and catalytic combustible gas sensors which include such pelements is found in Mosely, P. T. and Tofield, B. C., ed., *Solid State Gas Sensors*, Adams Hilger Press, Bristol, England (1987). Combustible gas sensors are also discussed generally in Firth, J. G. et al., *Combustion and Flame* 21, 303 (1973) and in Cullis, C. F., and Firth, J. G., Eds., *Detection and Measurement of Hazardous Gases*, Heinemann, Exeter, 29 (1981).

Bead 30 will react to phenomena other than catalytic oxidation that can change its output (i.e., anything that changes the energy balance on the bead) and thereby create errors in the measurement of combustible gas concentration. Among these phenomena are changes in ambient temperature, humidity, and pressure.

To minimize the impact of secondary effects on sensor output, the rate of oxidation of the combustible gas may, for example, be measured in terms of the variation in resistance of sensing element or pelement 40 relative to a reference resistance embodied in an inactive, compensating element or pelement 50. The two resistances may, for example, be part of a measurement circuit such as a Wheatstone bridge circuit as illustrated in FIG. 1C. The output or the voltage developed across the bridge circuit when a combustible gas is present provides a measure of the concentration of the combustible gas. The characteristics of compensating pelement 50 are typically matched as closely as possible with active or sensing pelement 40. In a number of systems, compensating pelement 50 may, however, either carry no catalyst or carry an inactivated or poisoned catalyst. In general, changes in properties of compensating elements caused by changing ambient conditions are used to adjust or compensate for similar changes in the sensing element.

Catalytic combustible gas sensors are typically used for long periods of time over which deterioration of the sensing element or the like and malfunction of circuits may occur. A foreign material or contaminant such as an inhibiting material or a poisoning material (that is, a material which inhibits or poisons the catalyst of the sensing element) may, for example, be introduced to the sensing element. Contaminants are deposited upon the surface of an element from the environment. If the element is heated to a certain temperature, many such materials react (for example, oxidize—either partially or completely) upon the surface of the element. Such reaction may result in a species that is more strongly bound to the surface. An inhibiting, contaminant material typically will "burn off" over time, but a poisoning, contaminant material permanently destroys catalytic activity of a sensing element. Inhibiting materials and poisoning materials are sometimes referred to herein collectively as "contaminants" or "contaminant material." Often, it is difficult to determine such an abnormal operational state or status of a combustible gas sensor without knowingly applying a test gas to the combustible gas sensor. In many cases, a detectible concentration of a combustible gas analyte in the ambient environment is a rare occurrence. Testing of the operational status of a combustible gas sensor typically includes the application of a test gas (for example, a gas including a known concentration of the analyte or a simulant thereof to which the combustible gas sensor is similarly responsive) to the sensor. Periodic testing using a combustible gas may, however, be difficult, time consuming and expensive.

Problems associated with contamination and/or degradation of the catalyst structures in combustible gas sensors are well known. Sulfur-containing compounds (inhibitors) have been known to target and inhibit the catalyst structures. Filtering techniques are generally used to prevent their passage into the structure. If they do enter the structure, they are bound until a sufficient level of heat is applied to promote their release or decomposition. Volatile silicon/organosilicon compounds (poisons) are also known to cause significant issues with catalytic structures as they are permanently retained, and eventually result in the total inactivity of the catalyst. Further, high levels of hydrocarbons can also deposit incomplete and/or secondary byproducts such as carbon within the structure. Lead compounds, organophosphates and halogenated hydrocarbons are also known to poison/inhibit catalysts used in combustible gas sensors.

Manufacturers may add a layer of inhibitor/poison (contaminant) absorbing material outside of the supported catalyst of a sensing element as well as a compensating element. However, exposure to a sufficient amount of inhibitor/poison can still render the catalyst inactive. Moreover, increasing the mass of the sensing/compensating element increases the power requirements of the sensor, which may be undesirable, particularly in the case of a portable or other combustible gas sensor in which battery power is used.

An inhibited or poisoned sensing element may go undetected by, for example, high sensitivity bridge and other circuits used in combustible gas sensors. Users have long reported cases where their catalytic sensors are reading zero (that is, the bridge circuitry is balanced), yet the sensors show little response to gas challenges. A notable example of this effect occurs when an organosilicon vapor such as hexamethyldisiloxane (HMDS) is introduced to the sensor. The HMDS will indiscriminately diffuse into the sensor housing and surroundings, adsorb onto the surface of the detector and/or compensator, and oxidize into a layer of silica (silicon dioxide or $SiO_2$) or $Si_xC_yO_z$ species. Since both elements are typically operated at similar temperatures, silicone deposition occurs at an equal rate, keeping the bridge in balance. Unfortunately, this renders the elements permanently inactive. Indeed, some manufacturers use this poisoning process to manufacture compensating elements or compensators for combustible gas sensors.

A number of methods and systems have been developed in an attempt to sense inhibition/poisoning (contamination) of a catalytic sensing element with limited success. In general, such methods monitor for a change in properties of the catalytic structure of the gas sensing element over time. It remains desirable to develop diagnostic systems and methods for catalytic sensors and structures to detect inhibition/poisoning.

SUMMARY

In one aspect, a system for detecting an analyte gas in an environment includes a first gas sensor, a first contaminant sensor separate and spaced from the first gas sensor, and electronic circuitry in electrical connection with the first gas sensor to determine if the analyte gas is present based on a response of the first gas sensor. The electronic circuitry is further in electrical connection with the first contaminant sensor to measure a response of the first contaminant sensor over time. The measured response of the first contaminant sensor varies with an amount of one or more contaminants to which the system has been exposed in the environment over time. The first gas sensor may, for example, be a first combustible gas sensor.

In a number of embodiments, the first contaminant sensor includes a first contaminant sensor element separate and spaced from the first combustible gas sensor. The first contaminant sensor element includes a first electrically conductive heating component and a first interface structure on the first electrically conductive heating component. The electronic circuitry may, for example, be configured to provide energy to the first electrically conductive heating component. In a number of embodiments, the measured response is a thermodynamic response of the first contaminant sensor element which varies with mass of the one or more contaminants deposited on the first interface structure thereof.

The first combustible gas sensor may, for example, include a first element including a first electrically conductive heating element, a first support structure on the first electrically conductive heating element and a first catalyst supported on the first support structure. The electronic circuitry may, for example, be configured to provide energy to the first electrically conductive heating element to heat the first element to at least a first temperature at which the first catalyst catalyzes combustion of the analyte gas and to determine if the analyte gas is present based on the response of the first combustible gas sensor while the first element is heated to at least the first temperature.

In a number of embodiments, the first contaminant sensor further includes a second contaminant sensor element. The second contaminant sensor element may include a second electrically conductive heating component and a second interface structure on the second electrically conductive heating component. The electronic circuitry may, for example, be configured to operate the second contaminant sensor element as a compensating element for at least the first contaminant sensor element to compensate for ambient conditions. In a number of embodiments, the second contaminant sensor element is treated to be generally insensitive to at least one of the one or more contaminants. The second contaminant sensor element may, for example, be treated with a predetermined amount of an oxidized organosilicon compound.

In a number of embodiments, the first interface structure is selected to adsorb at least one of the one or more contaminants that undergo oxidation upon heating. The first interface structure may, for example, include an oxide. In a number of embodiments, the first interface structure includes a silicon oxide or a metal oxide. The first interface structure may, for example, have a surface area of at least 75 $m^2/g$. The first interface structure may, for example, include a refractory metal oxide. The first interface structure may, for example, include aluminum oxide, tin oxide, zinc oxide or copper oxide.

In a number of embodiments, the first contaminant sensor element includes no metal catalyst. The first contaminant sensor element may, for example, consists essentially of the first electrically conductive heating component and the first interface structure, which consists essentially of an oxide.

In a number of embodiments, the system further includes a first filter pathway between the first gas sensor and the environment. The first filter pathway has a first capacity to remove at least one of the one or more contaminants. The system further includes a second filter pathway between the first contaminant sensor and the environment. The second filter pathway has a second capacity to remove at least one of the one or more contaminants. The second capacity is less than the first capacity. In a number of embodiments, the first capacity includes a first adsorbent filtration capacity and the second capacity includes a second adsorbent filtration capacity, less than the first adsorbent filtration capacity.

In a number of embodiments, the system includes a first filter pathway between the first element of the first combustible gas sensor and the environment, which has a first capacity to remove at least one of the one or more contaminants, and a second filter pathway between the first contaminant sensor element and the environment, which has a second capacity to remove at least one of the one or more contaminants, wherein the second capacity is less than the first capacity. As set forth above, the first capacity may include a first adsorbent filtration capacity, and the second capacity may include a second adsorbent filtration capacity, less than the first adsorbent filtration capacity. In a number of embodiments, the second adsorbent filtration capacity is zero.

In a number of embodiments, the first element of a first combustible gas sensor hereof is low-thermal-mass element. The first element of the first combustible gas sensor may, for example, a thermal time constant less than 8 seconds or less than 1 second. The first element of the first combustible gas sensor may, for example, be a MEMS element. The first element of the first combustible gas sensor may, for example, be a low-thermal-mass pelement.

In a number of embodiments, the first contaminant sensor element is low-thermal mass element. The first contaminant sensor element may, for example, have a thermal time constant less than 8 seconds of less than 6 second. In a number of embodiments, the first contaminant sensor element is a low-thermal-mass pelement.

In a number of embodiments, a pulse is applied to the first contaminant sensor element in which energy to the first contaminant sensor element is increased or decreased to induce the measured response from the first contaminant sensor element. The electronic circuitry may, for example, be configured to analyze the measured response.

In a number of embodiments, a temperature of the second contaminant sensor element is maintained below a temperature at which at least one or the one or more contaminants is oxidized on the second interface structure. The temperature of the second contaminant sensor element may, for example, be maintained below 150° C. or below 90° C.

The temperature of the first contaminant sensor element may, for example, be increased via an applied pulse to induce joule heating and for sufficient time to raise the temperature of the first contaminant sensor element. In a number of embodiments, energy is decreased via an applied pulse from a temperature of at least the first temperature such that convective heat transfer between the first interface structure and surrounding gas ceases, and for sufficient time so that the temperature of the first contaminant sensor element decreases below the temperature at which joule heating of the first contaminant sensor element occurs.

In a number of embodiments, the electronic circuitry is configured to apply a plurality of pulses to the first contaminant sensor element over time in which energy to the first element is increased or decreased to induce the measured response from the first contaminant sensor element in each of the plurality of pulses. The electronic circuitry may, for example, be configured to analyze one or more of the measured responses.

In a number of embodiments, the electronic circuitry is configured to adjust an output associated with a response of the combustible gas sensor based upon the measured response of the first contaminant sensor.

In another aspect, a method for detecting an analyte gas in an environment includes providing a first gas sensor, providing a first contaminant sensor separate and spaced from the first gas sensor, providing electronic circuitry in electrical connection with the first gas sensor and with the first contaminant sensor, measuring a response of the first gas sensor to determine via the electronic circuitry if the analyte gas is present, and measuring a response of the first contaminant sensor to determine via the electronic circuitry if the system has been exposed to one or more contaminants. The measured response of the first contaminant sensor varies with an amount of one or more contaminants to which the system has been exposed in the environment over time.

In a number of embodiments, the first gas sensor is a first combustible gas sensor. The first contaminant sensor may, for example, include a first contaminant sensor element separate and spaced from the first combustible gas sensor. The first contaminant sensor element includes a first electrically conductive heating component and a first interface structure on the first electrically conductive heating component. The electronic circuitry is configured to provide energy to the first electrically conductive heating component. The measured response of the first contaminant sensor is a thermodynamic response of the first contaminant sensor element which varies with mass of the one or more contaminants deposited on the first interface structure thereof.

In a number of embodiments, the first combustible gas sensor includes a first element including a first electrically conductive heating element, a first support structure on the first electrically conductive heating element and a first catalyst supported on the first support structure. The electronic circuitry may, for example, be configured to provide energy to the first electrically conductive heating element to heat the first element to at least a first temperature at which the first catalyst catalyzes combustion of the analyte gas and to determine if the analyte gas is present based on the response of the first combustible gas sensor while the first element is heated to at least the first temperature.

In a number of embodiments, the first contaminant sensor further includes a second contaminant sensor element. The second contaminant sensor element may, for example, include a second electrically conductive heating component and a second interface structure on the second heating electrically conductive heating component. The method may further include operating the second contaminant sensor element via the electronic circuitry as a compensating element for at least the first contaminant sensor element to compensate for ambient conditions.

In a further aspect, a system includes electronic circuitry comprising a control system, a primary combustible gas sensor in electrical connection with the electronic circuitry to determine if an analyte gas is present based on a response of the primary combustible gas sensor and a trigger combustible gas sensor in electrical connection with the electronic circuitry to determine if the analyte gas is present based on a response of the trigger combustible gas sensor. The electronic circuitry is configured to operate the trigger combustible gas sensor to detect a value of a response at or above a threshold value. The primary combustible gas sensor is activated from a low-power state upon the threshold value being detected by the trigger combustible gas sensor. The system further includes a first contaminant sensor in electrical connection with the electronic circuitry, which is positioned separate and spaced from the primary combustible gas sensor and from the trigger combustible gas sensor. The electronic circuitry is further configured to measure a response of the first contaminant sensor over time. The measured response of the first contaminant sensor varies with an amount of one or more contaminants to which the system has been exposed in the environment over time.

In a number of embodiments, the primary combustible gas sensor includes a first primary element in operative connection with the electronic circuitry and including a first primary support structure, a first primary catalyst supported on the first primary support structure and a first primary heating element in operative connection with the first primary support structure. The trigger combustible gas sensor may, for example, include a first trigger element of low-thermal-mass in operative connection with the electronic circuitry. The first trigger element may, for example, include a first trigger heating element, a first trigger support structure and a first trigger catalyst supported on the first trigger support structure.

In a number of embodiments, the first contaminant sensor includes a first contaminant sensor element separate and spaced from the primary combustible gas sensor and the trigger combustible gas sensor. The first contaminant sensing element may, for example, include a first electrically conductive heating component and a first interface structure on the first electrically conductive heating component. The electronic circuitry may, for example, be configured to provide energy to the first electrically conductive heating component.

In a number of embodiments, the system further includes a first filter pathway between the trigger combustible gas sensor and the environment. The first filter pathway may, for example, have a first capacity to remove at least one of the one or more contaminants. The system may further include a second filter pathway between the primary combustible gas sensor and the environment. The second filter pathway may, for example, have a second capacity to remove at least one of the one or more contaminants. The system may further include a third filter pathway having a third capacity between the first contaminant sensor and the environment. The third capacity is less than the first capacity and less than the second capacity. In a number of embodiments, the second capacity is less than the first capacity. The first capacity may, for example, include a first adsorbent filtration capacity. The second capacity may, for example, include a second adsorbent filtration capacity. The third capacity may, for example, include a third adsorbent filtration capacity. In a number of embodiments, the third adsorbent filtration capacity is zero.

The present devices, systems, and methods, along with the attributes and attendant advantages thereof, will best be appreciated and understood in view of the following detailed description taken in conjunction with the accompanying drawings.

BRIEF DESCRIPTION OF THE DRAWINGS

FIG. 7 illustrates methane sensitivity as a function of time in contaminant exposure for sensors including filter elements or components for contaminants including HDMS which were tested in 15 ppm HMDS at standard run temperature FIG. 8 illustrates a light-off curve for hexamethyldisiloxane (HMDS) via sensitivity loss in methane of a catalytically active analyte sensing element as a function of exposure temperature in HMDS.

DETAILED DESCRIPTION

Figure 1B:
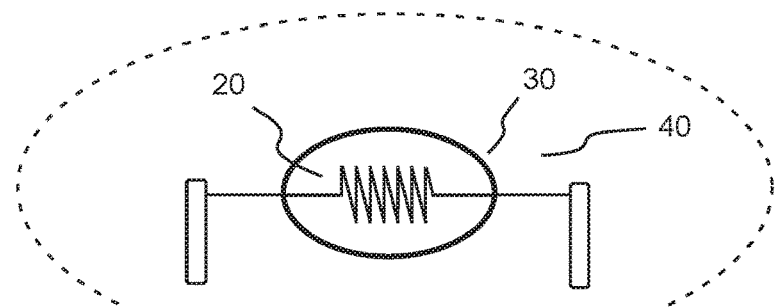
FIG. 1B illustrates an enlarged view of the active sensing element, pelement or detector of the combustible gas sensor of FIG. 1A.
Figure 1A:
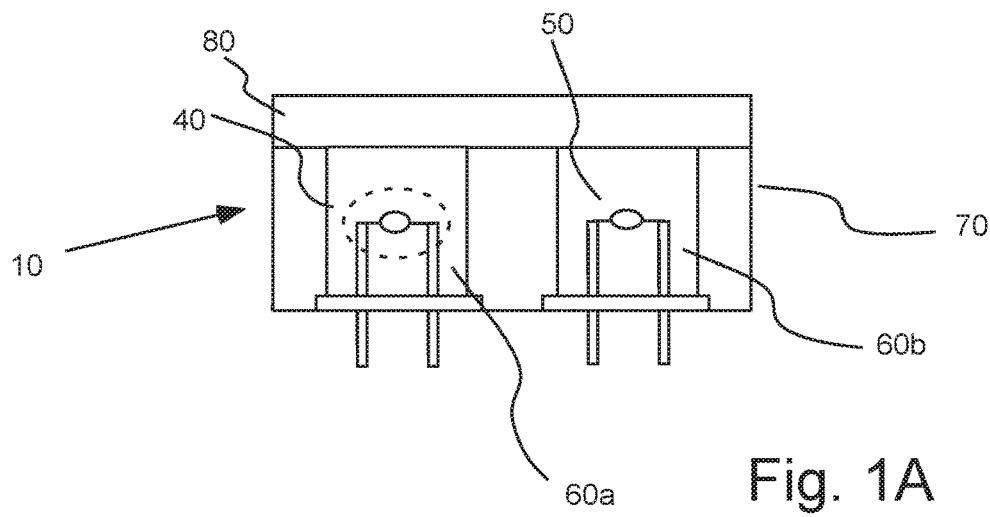
FIG. 1A illustrates an embodiment of a currently available combustible gas sensor.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etcetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "a sensing element" includes a plurality of such sensing element and equivalents thereof known to those skilled in the art, and so forth, and reference to "the sensing element" is a reference to one or more such sensing elements and equivalents thereof known to those skilled in the art, and so forth.

The terms "electronic circuitry", "circuitry" or "circuit," as used herein includes, but is not limited to, hardware, firmware, software or combinations of each to perform a function(s) or an action(s). For example, based on a desired feature or need. a circuit may include a software controlled microprocessor, discrete logic such as an application specific integrated circuit (ASIC), or other programmed logic device. A circuit may also be fully embodied as software. As used herein, "circuit" is considered synonymous with "logic." The term "logic", as used herein includes, but is not limited to, hardware, firmware, software or combinations of each to perform a function(s) or an action(s), or to cause a function or action from another component. For example, based on a desired application or need, logic may include a software controlled microprocessor, discrete logic such as an application specific integrated circuit (ASIC), or other programmed logic device. Logic may also be fully embodied as software.

The term "processor," as used herein includes, but is not limited to, one or more of virtually any number of processor systems or stand-alone processors, such as microprocessors, microcontrollers, central processing units (CPUs), and digital signal processors (DSPs), in any combination. The processor may be associated with various other circuits that support operation of the processor, such as random access memory (RAM), read-only memory (ROM), programmable read-only memory (PROM), erasable programmable read only memory (EPROM), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

The term "controller," as used herein includes, but is not limited to, any circuit or device that coordinates and controls the operation of one or more input and/or output devices. A controller may, for example, include a device having one or more processors, microprocessors, or central processing units capable of being programmed to perform functions.

The term "logic," as used herein includes, but is not limited to. hardware, firmware, software or combinations thereof to perform a function(s) or an action(s), or to cause a function or action from another element or component. Based on a certain application or need, logic may, for example, include a software controlled microprocess, discrete logic such as an application specific integrated circuit (ASIC), or other programmed logic device. Logic may also be fully embodied as software. As used herein, the term "logic" is considered synonymous with the term "circuit."

The term "software," as used herein includes, but is not limited to, one or more computer readable or executable instructions that cause a computer or other electronic device to perform functions, actions, or behave in a desired manner. The instructions may be embodied in various forms such as routines, algorithms, modules or programs including separate applications or code from dynamically linked libraries. Software may also be implemented in various forms such as a stand-alone program, a function call, a servlet, an applet, instructions stored in a memory, part of an operating system or other type of executable instructions. It will be appreciated by one of ordinary skill in the art that the form of software is dependent on, for example, requirements of a desired application, the environment it runs on, or the desires of a designer/programmer or the like.

In a number of representative embodiments hereof, one or more contaminant sensors hereof are combined with or incorporated with one or more combustible gas sensors. However, the contaminant sensors hereof are beneficial for use with any sensor or multi-sensor system having an element or component which is sensitive to mass deposition of one or more contaminants thereon as discussed further below. In general, such a contaminant or contaminants is/are compositions other than the analyte or target composition(s) for the sensor or sensor system. Such a contaminant may, for example, degrade the performance of a sensor or sensor system in one or more manners. In a number of embodiments, the elements or components of a sensor or sensor system upon which one or more contaminants may deposit are heated elements or components (for example, a sensing element, an energy source etc.) which are heated to a temperature at which one or more adsorbed/chemisorbed contaminants react to bind with a surface of the element or component. In other embodiments, such elements or components include, for example, a filter material upon which one or more contaminant may deposit. One or more contaminants may, for example, be an interferent for the sensor (that is, a composition to which the sensor exhibits cross-sensitivity), an inhibitor, a poison, etc. Representative sensors with which the contaminant sensors hereof may be used in combination include, but are not limited to, combustible gas sensors, metal oxide sensors (MOS), solid state oxygen sensors, photoionization detectors (PIDs), and electrochemical sensors. One or more contaminant sensors hereof may, for example, be positioned within a common housing with one or more such sensors.

In a number of representative embodiments hereof, devices, systems and methods of determining the well-being or operational status of a one or more components (for example, a sensing element including a catalytic structure and/or a filter) in a sensor such as a combustible gas sensor via a separate, contaminant sensor are set forth. The devices, systems and methods hereof do not require the use or application of a test gas or any other gas to the sensor in determining contaminant exposure. A test gas is a gas which includes a non-zero known concentration of the analyte (or target) gas or a simulant thereof. In the devices, systems and methods hereof, a contaminant sensor (including, for example, a contaminant sensing element or detector), which is physically separate from any analyte or target gas sensing element or any compensating element, is provided. Contaminant sensing elements hereof may, for example, include a heating component or element (typically a conductive component or element) and an interface structure disposed on the heating component or element. Contaminants are deposited/adsorbed/chemisorbed upon the surface of the interface structure, and certain contaminants (for example, sulfur compounds and silicon/organosilicon compounds) may become strongly bound thereto upon heating/reaction. In a number of embodiments, the interface structure includes an oxide, which may be a refractory or heat-resistant material (for example, a refractory metal oxide). In a number of embodiments, the interface structure has a surface area of at least 75 m²/g, or a surface area of at least 150 m²/g.

During the application of low voltages (for example, 0V-0.25V), to a heating element wire or coil such as coil 20 (that is, a heating element or component), the element resistance remains consistent. In such a voltage range, resistive changes are predominantly governed by ambient temperature fluctuations. The principles employed in this regime are well known and are used, for example, in resistive thermometers. In that regard, the platinum resistance thermometer is a versatile instrument for temperature measurement in the range from approximately −200° C. to +1000° C. One may, for example, use the simplified Callendar—Van Dusen equation to determine the temperature dependent resistance as follows:

$$R_t = R_0[1+\alpha(t-t_0)]$$

wherein $R_t$ is the resistance of the element at temperature t, $R_0$ is the resistance at a standard temperature to, and a is the temperature coefficient of resistance. The above principle may, for example, be used as described in U.S. Pat. No. 8,826,721, the disclosure of which is incorporated herein by reference, to operate an element of a combustible gas sensor (which may be a catalytically active sensing element or a catalytically inactive element) in a low power (voltage), low-temperature mode in which the element is able to function as a compensating element or compensator.

The application of higher voltages (for example, >0.5V) will cause the heating element or component to increase in temperature, and thus in resistance. This effect is known as Joule's first law or the Joule-Lenz law. Joule heating, also known as ohmic heating or resistive heating, is the process by which the passage of an electric current through a conductor releases heat. In the case of, for example, an analyte element including a catalyst support structure or a contaminant sensing element hereof including an interface structure, the heat transfer from the heating element/component will eventually reach an equilibrium as the heat will conduct from the heating element to the structure overlaying the heating element (including, for example, an oxide or refractory material and any catalyst supported thereon) and then via fluidic convection through the surrounding gases. Thermal equilibrium will remain balanced until (a) the ambient temperature changes; (b) the makeup of the surrounding gas mixture is altered, or (c) the transfer of heat between the wire and the mass of the element changes (as a result of a mass or density change). These effects are all competing and interacting effects.

In the case of a combustible gas sensor, a heating element such as heating element 20 of FIG. 1B (for example, a conductive wire, coil or surface) is used to sufficiently raise the structure of the element (including the support structure and catalyst) to a temperature to promote the catalytic reaction of the analyte or target gas. As used herein with respect to an element hereof (that is, an analyte sensing element or analyte element, a compensating element or a contamination sensing element), temperature refers to an average temperature over the volume of the element. Heating elements or components have generally been made from coils, and over time smaller diameter wires have been used to reduce the power consumption of the element.

Figure 2A:
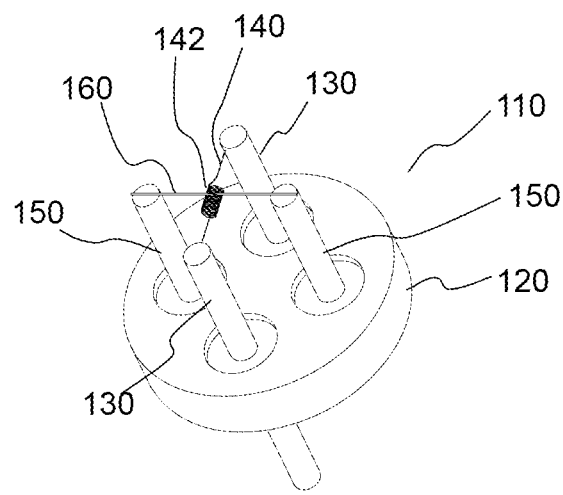
FIG. 2A illustrates a perspective view of an embodiment of a detector assembly wherein a sensing element is supported by a conductive supporting wire.
Figure 2B:
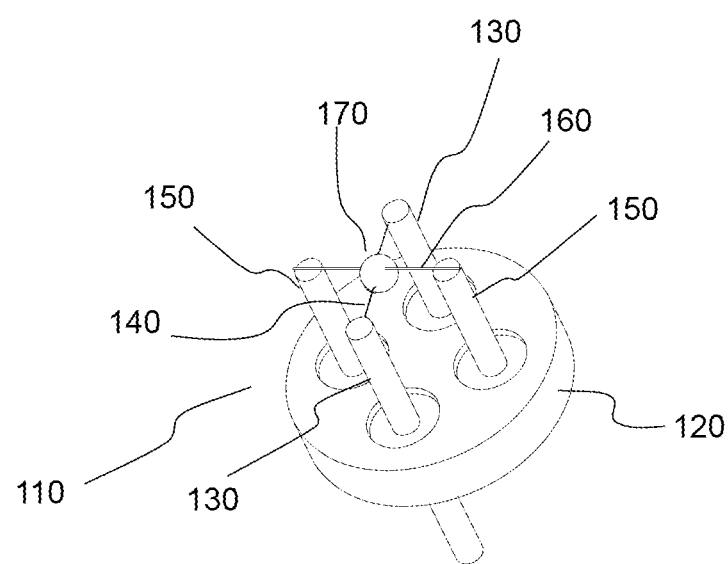
FIG. 2B illustrates a perspective view of the detector assembly of FIG. 2A including a ceramic bead (upon which a catalyst is supported) formed over the sensing element wire.
Figure 2C:
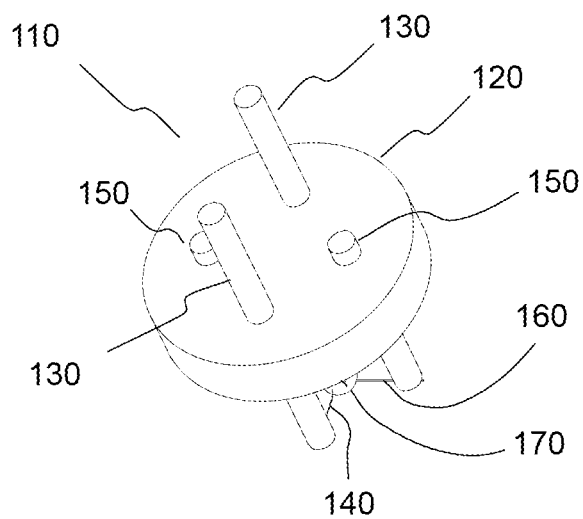
FIG. 2C illustrates another perspective view (generally opposite that of FIG. 2B) of the detector assembly of FIG. 2A.

The use of conductive elements or components such as wires having relatively small diameter in element for combustible gas sensors is, for example, disclosed in U.S. Pat. No. 8,826,721 and U.S. Patent Application Publication No. 2018/0128763, the disclosure of which is incorporated herein by reference. In that regard, FIGS. 2A through 2C illustrate a representative embodiment of a detector/element assembly 110 which may, for example, be used in a combustible gas sensor. Element assembly 110 includes a base 120 to which two electrically conductive contact members 130 (extending members or posts in the illustrated embodiment) are attached. A sensing conductive element or heating element 140 is connected between contact members 130, wherein each end of conductive elements 140 is connected to or anchored to one of contact members 130. In the illustrated embodiment, conductive element 140 includes an intermediate section including a coiled section 142 that can, for example, be located approximately centrally between the ends of conductive element 140. Wires and/or other conductive elements for heating elements or components are selected to have a favorable temperature coefficient for sensing applications and are generally a precious metal or alloy.

Element assembly 110 further includes two support members 150 (extending members or posts in the illustrated embodiment) connected to base 120. In the illustrated embodiment, a support member or element 160 in the form of, for example, a wire, a ribbon, a rod or other suitable support structure or material extends between support members or posts 150. Base 120, contact members 130 and support members 150 can, for example, be formed of a metal such as KOVAR® (a nickel-cobalt ferrous alloy designed to be compatible with the thermal expansion characteristics of borosilicate glass) available from Carpenter Technology Corporation of Reading, Pa. Contact members 130 and support members 150 can, for example, be sealed to base 120 using a glass such as borosilicate glass to provide electrical isolation.

Using a strong yet relatively thin support element 160 anchored, connected or attached at each end thereof (for example, anchored at two support members or posts 150) prevents bead movement in all three dimensions while limiting heat loss. In the illustrated embodiment of FIGS. 2A through 2C, support element 160 passes through and contacts one of the coils of coiled section 142. Contact between support element 150 and conductive element 140 is thus minimal. As described below, support element 150 need not contact conductive element 140 to provide support therefor, but can contact or pass through a catalyst support member or structure 170 encompassing conductive element 140.

A balance may, for example, be established between the tensile strength and the thermal conductivity to achieve an effective result for support element 150. In general, a quotient or ratio calculated by dividing the tensile strength in units of pounds per square inch of psi by the thermal conductivity in units of watts/cm/° C. may, for example, be at least 250,000, at least 400,000 or even at least 500,000. For example, a support element in the form of a wire made from an alloy of platinum and tungsten may have a tensile strength of 250,000 psi and a thermal conductivity of 0.5 watts/cm/° C., resulting in a quotient of 500,000. For support elements having a higher tensile strength, a higher thermal conductivity may be acceptable since support elements of smaller average diameter (or average cross-sectional area) can be used (resulting in less mass to conduct heat away from the sensing element). Moreover, reducing the size/volume of the element reduces the effect of ambient humidity and pressure changes on the sensor. For example, in the case of a tungsten support element having a tensile strength of 600,000 psi and a thermal conductivity of 1.27 watts/cm/° C., a smaller average diameter support element can be used to achieve a similar result to that achieved with the platinum-tungsten alloy support element described above. Alternatively, one could also choose a support element of an alloy of platinum with 20% iridium having a larger average diameter. Such a platinum-iridium alloy has a tensile strength of 120,000 psi and a thermal conductivity of 0.18 watts/cm/° C. Metal support elements or metal alloy elements having the above-described properties can be used to maximize strength/support while minimizing heat loss.

In that regard, in several embodiments, support element 160 exhibits relatively high strength (for example, having a tensile strength of at least 100,000 psi, at least 250,000 psi, or even at least 400,000 psi) as well as low thermal conductivity (for example, having a thermal conductivity less than 1.5 less watts/cm/° C., less than 0.5 watts/cm/° C., no greater than 0.25 watts/cm/° C., or even no greater than 0.10 watts/cm/° C.) to provide a quotient as described above. In a number of embodiments, the average diameter of support element 160 (in the case of a support element of a generally circular cross-section) is in the range of approximately 0.0005 (12.7 µm) to 0.0025 inches (63.5 µm). In the case of support elements having a noncircular cross-section, the average cross-sectional area can, for example, be in the range of the average cross-sectional area of an element of generally circular cross-section having an average diameter in the range of approximately 0.0005 to 0.0025 inches. References herein to elements having a certain average diameter are also references to elements having a generally noncircular cross-section, but having an average cross-sectional area equivalent to the average cross-sectional area provided by the stated average diameter. In several representative studies, an in-molded wire was used as support element 160. In several such embodiments, a platinum-tungsten alloy support element 160 having an average diameter of approximately (that is, within 10% of) 0.001 inches (63.5 µm) provided a robust support and did not result in measurable additional power required to operate sensing element 140. Alloys of tungsten, nickel, molybdenum or titanium with, for example, platinum, palladium or rhodium can, for example, be used in support element 160.

As illustrated in FIG. 2B, catalyst support structure 170 (for example, a ceramic bead in a number of embodiments) can be formed on coil section 120 of sensing conductive element 140 to support a catalyst and form a sensing element/pelement. In forming catalyst support structure 170 as a refractory material such as a ceramic bead, an aluminum oxide suspension may, for example, be fired onto coiled section 142. The resultant catalyst support structure/ceramic bead 170 may be impregnated with a catalyst. Although a bare wire comprising a catalytic material (such as platinum) can be used as a sensing element in certain embodiments of a combustible gas sensor, a catalyst support structure 170 (such as a ceramic bead) provides increased surface area for one or more catalyst species.

In the embodiment illustrated in FIGS. 2A through 2C, catalyst support structure 170 is formed over (to encompass) conductive element 140 and support element 160. Support element 160 need not contact conductive element 140 to provide support therefor. For example, support element 160 can pass through or contact support structure 170 without contacting conductive element 140 and indirectly provide support for conductive element 140. To provide support for conductive element 140 in three dimensions, support element 160 preferably passes through catalyst support structure 170.

The support assembly, including, for example, support member 150 and support element 160, enables the use of a sensing element 140 having a relatively small average diameter. For example, a wiring having an average diameter no greater than approximately 20 µm of 10 µm may be used. Such a small average diameter wire (with a corresponding higher per unit length resistance than larger diameter wires) lends itself well to reducing the required operating current (which is very desirable in portable applications), and thus the required power levels. In a number of embodiments, the support members or catalyst support members hereof have a volume less than $6.5 \times 10^7$ µm$^3$, less than $4.46 \times 10^7$ µm$^3$, or even than $1.4 \times 10^7$ µm$^3$.

As known in the art, a heating element in the form of a wire or wire coil may be dipped it into an aqueous suspension of a precursor of a refractory. The precursor may then be converted into the refractory material by heating (for example, by the passage of an electrical heating current through the heating element). The dipping process is usually repeated to build up a support structure of the desired size/average diameter around the heating element. In forming a catalytically active element, a solution or dispersion of a catalyst may then be applied to the outer surface of the support structure.

Low thermal time constants associated with low thermal mass sensors such as the low-thermal-mass pelements described above assist in providing quick response times, reducing the time an element may be unavailable for use in a detection mode and decrease power requirements. Low-thermal-mass elements hereof may, for example, have a thermal time constant of 8 second or less, 6 seconds or less, 1 second or less, 0.5 seconds or less or 0.250 second or less. A low thermal mass/low thermal time constant sensor may, for example, be a pelement of low thermal mass as described above or a microelectronic mechanical systems (MEMS) element to provide a thermal time constant. As used herein the thermal time constant of an element is defined as the time required to change 63.2% of the total difference between its initial and final temperature when subjected to a step function change in drive power, under zero power initial conditions. MEMS elements typically have a lower thermal time constant than low-thermal-mass pelements. MEMS elements may, for example, have thermal time constants of 1 second or less, 0.5 seconds or less or 0.250 second or less.

Oxidation catalysts formed onto a helical wire heater as described above are typically referred to as pelements, while those formed onto hotplates (whether MEMS hotplates or conventional, larger hotplates) are sometimes known by the substrate. Oxidative catalysts formed on MEMS heating elements are sometimes referred to as MEMS pellistors. As used herein, the term "MEMS pellistor" or "MEMS element" refers to a sensor component with dimensions less than 1 mm that is manufactured via microfabrication techniques. In a number of representative embodiments, sensing elements formed as MEMS pellistors hereof may be manufactured with a thick film catalyst, powered to an operating temperature by resistive heating and are used to detect combustible gases. In a number of representative embodiments, the thickness and diameter for a MEMS catalyst film is approximately 15 microns and approximately 650 microns, respectively.

Figure 3A:
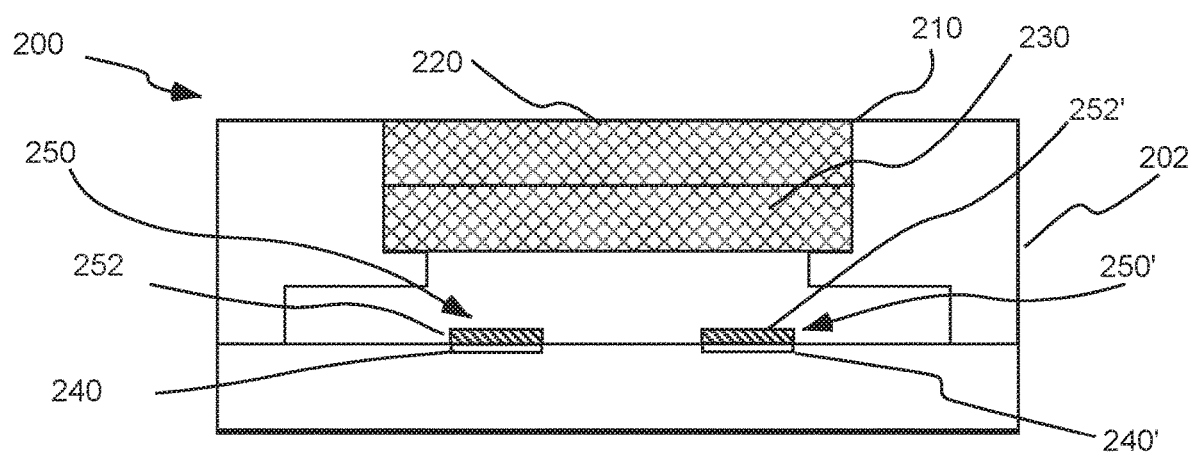
FIG. 3A illustrates schematically a cross-sectional view of an embodiment of a low-thermal mass, MEMS hotplate combustible gas sensor suitable for use herein.
Figure 3B:
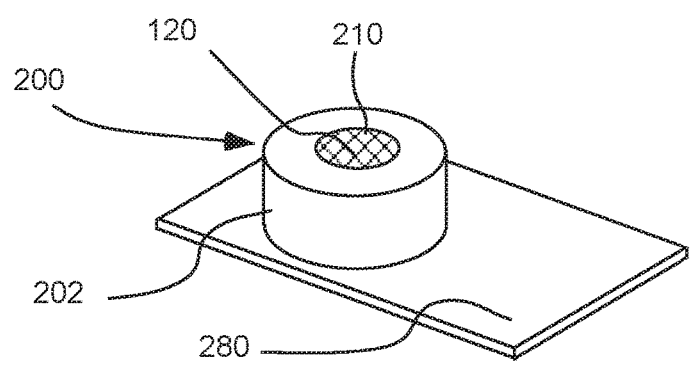
FIG. 3B illustrates a perspective view of the low-thermal-mass combustible gas sensor of FIG. 3A in operative connection with a printed circuit board.

FIG. 3A illustrates a cutaway view of an embodiment of a MEMS or micro-hotplate sensor 200 hereof, which includes a housing 202 having a gas inlet 210. A screen or cap 220, which may include or function as a filter 230, may, for example, be placed in connection with inlet 210. The energy (current and voltage) used in MEMS micro-hotplate sensor 200 may, for example, be sufficiently low to provide intrinsic safety such that a flashback arrestor, as known in the combustible gas detector arts, may not be necessary. As described above, flashback arrestors (for example, porous frits) allow ambient gases to pass into a housing but prevent ignition of combustible/flammable gas in the surrounding environment by hot elements within the housing. One or more heating elements or hotplates 240 may, for example, be used to heat an oxidative layer 252 (which may, for example, be an oxidative catalyst layer) of a first MEMS element or pellistor 250 to a first operating temperature. In a number of embodiments, a second MEMS element or second pellistor 250' may be included within MEMS hotplate trigger sensor 200 to be heated to a second operating temperature.

In a number of embodiments, first MEMS element 250 may be operated as a sensing or detecting element and second MEMS element 250' may be operated as a compensating element as known in the combustible gas sensor arts. In other embodiments, as further described below, the function of MEMS elements 250 and 250' which each include an active catalyst layer may be switched between analyte sensing and compensating by altering the mode of operation thereof.

Typically, compensating elements include a deactivated catalyst layer or other deactivation layer which destroys the activity of the compensating element to oxidize combustible analyte gases. Such inactive compensating elements are typically operated at the same temperature of the analyte element. As described in U.S. Pat. No. 8,826,721, the operation of a particular element as a sensing element or a compensating element may be controlled by controlling the operating temperature thereof. If the operating temperature of an element is maintained at or above a temperature at which gas will combust at the surface thereof, it may be operated as a sensing element. If the operating temperature of an element is maintained below a temperature at which gas will combust at the surface thereof, it may be operated as a compensating element. The temperature at which gas will combust at the surface of an element depends upon the composition of that surface. Surfaces including a catalytic material will typically cause combustion at a temperature (a catalytic light-off temperature) lower than a surface not including a catalytic material. An element including a catalytic material may be alternated between use as a sensing element and use as a compensating element through control of the operating temperature thereof (that is, between a higher temperature operational/sensing mode and a lower temperature/compensating mode).

If operated solely as a MEMS compensator element 250' may, for example, include an inactive layer 252' which may be heated by one or more heating elements or hotplates 240'. In this case, the second operating temperature may be maintained at a temperature lower than the temperature required to cause combustion at a surface thereof in the absence of a catalyst. Alternatively layer 252' may include an active catalyst and be operated at a sufficiently low temperature to prevent catalytic oxidation of combustible gas at the surface thereof. The second temperature may, for example, be ambient temperature.

Figure 1C:
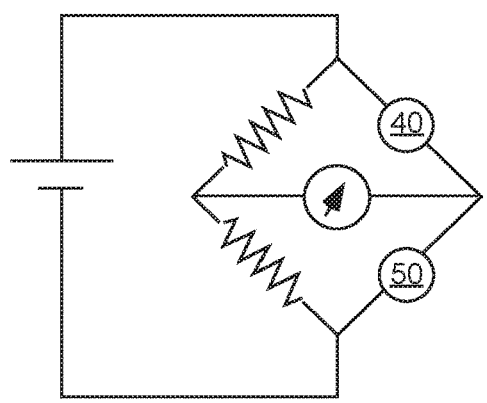
FIG. 1C illustrates an embodiment of circuitry for the combustible gas sensor of FIG. 1A.

MEMS hotplate sensor 200 may, for example, mounted on a printed circuit board or PCB 280. The two resistances of the element 250 and element 250' may, for example, be part of a measurement circuit such as a Wheatstone bridge circuit as illustrated in FIG. 1C or a simulated Wheatstone bridge circuit. A representative example of a MEMS hotplate sensor suitable for use herein is an SGX MP7217 hotplate sensor or pellistor available from SGX Sensortech, SA of Corcelles-Coromondreche, Switzerland. Such a MEMS hotplate sensor is disclosed, for example, in U.S. Pat. No. 9,228,967, the disclosure of which is incorporated herein by reference. MEMS technology, thin/thick film system technology, or other suitable micro- or nanotechnology may be used in forming low-thermal-mass elements for use herein. See, for example, U.S. Pat. Nos. 5,599,584 and/or 6,705,152, the disclosures of which are incorporate herein by reference.

As described above, the operation of a catalytic combustible gas sensor may proceed through electrical detection of the heat of reaction of a combustible gas on the oxidation catalyst (for example, through a resistance change via a Wheatstone bridge). The oxidation catalysts may, for example, operate in the temperature range of 350-600° C. for methane detection. Among common hydrocarbons, methane requires the highest temperature for combustion, hydrogen requires low temperatures, and larger alkanes fall in between, with longer to shorter carbon chain requiring lower to higher light-off temperatures.

The analyte elements, compensating elements and/or contaminant sensing elements hereof may be operated in either a comparative/continuous mode or in a dynamic mode. The amount of contaminant deposited upon a contaminant sensing element hereof may be relatable to, or correlated with, an amount or dosage (that is, exposure of a certain concentration over a certain period of time—for example, in the units of ppm-hour) of one or more contaminants experienced by a device or system hereof (and/or one or more components thereof) over time.

In a number of representative embodiments, comparative methods or measurements are used in determining deposition of contaminants on a contaminant sensing element. One skilled in the art appreciates that a number of different variables related to or relatable to a change in thermal properties of a contaminant sensing element hereof associated with a change in mass of the element may be used. Changes in one or more such variables are, for example, related to or indicative of a change in mass resulting from the presence of a contaminant on the interface structure of the contaminant sensing element. In a number of embodiments, changes in an electrical property (for example, resistance) of a conductive heating element of a contaminant sensing element associated with changes in the thermal properties of the contaminant sensing element are monitored. A variable such as voltage, current or resistance may, for example, be measured depending upon the manner in which the electrical circuitry of a sensor or instrument hereof is controlled. For example, voltage or current in an electronic circuit can be measured and related to a change in resistance of a contaminant sensing element. Alternatively, electronic circuitry of a sensor may be driven to maintain resistance of the contaminant sensing element relatively constant and a voltage or a current may be measured.

In the case of a comparative or continuous mode of operation, an element may, for example, be operated at a generally constant voltage, a constant current or a constant resistance (and thereby at a constant temperature) as described above during a particular mode of operation. To operate in a constant voltage, a constant current or a constant resistance mode, closed loop control is used.

In an open-loop control methodology wherein temperature varies over the interrogation period, one may use a variety of dynamic, pulsed, or modulated operations in the devices, systems and methods hereof. In a "dynamic-mode" or "dynamic interrogation mode" operational mode hereof, an element is, for example, briefly energized or de-energized via a change in the electric current flowing therethrough. The length of time of such dynamic interrogation pulses or changes may, for example, be very short in the case of low-thermal-mass elements. Once again, the elements hereof may (but need not) have a low thermal mass as described above. During an individual energy change or pulse, an element hereof experiences transitions through different thermal states as the temperature thereof changes over time. In a number of embodiments hereof, an interrogation method may be based on the observation of the non-linear electrical response in the electronic circuitry hereof, of which a catalyst support structure (and the catalyst supported thereon) or an interface structure is a part, as the non-linear thermodynamic action in the element transitions from one thermal state (and temperature) to another. A support structure or an interface structure that has become contaminated with poisons or inhibitors will exhibit a measurably different electrical response to a change in energy supplied thereto because of the different thermal properties resulting from the contamination. In a number of embodiments, interrogations are based on the measurement of dynamic action of a thermally transitioning structure and its associated electrical signals, which stands in contrast to other interrogation methods rooted in static analysis of steady-state signals. A dynamic interrogation pulse (in which applied energy is increased or decreased over a defined period of time) may be applied to an element that is otherwise operating in a continuous mode, wherein energy/temperature is maintained relative constant in one or more modes thereof, or in pulse-mode or pulse width modulation operation as described below. Like other interrogations methods hereof, dynamic interrogation measurements may be carried out in the ambient atmosphere (for example, air) without the application of a calibration gas, test gas or other gas. Dynamic interrogation measurements may, for example, be more sensitive to deposition of contaminants than steady-state or comparative measurements.

A dynamic-mode baseline response may first be established when there is high confidence that the element or elements have not been contaminated (for example, may be determined at the time of manufacture). A device may subsequently be placed in the dynamic-mode interrogation as described above to determine if contamination (poisoning/inhibition) has occurred. One or more threshold values may, for example, be established for slope of the curve, shape of the curve, area under the curve, or values at one or more times along the curve. Once again, such interrogations may, for example, occur periodically over time. The control system of the sensor systems hereof may automatically initiate such a dynamic-mode interrogation on a periodic or other basis. Moreover, a dynamic-mode interrogation may also be initiated manually.

In the case of dynamic mode interrogation, using an element having a relatively low thermal time constant enables decreasing or minimizing the length of the dynamic mode interrogation and the power used therein as compared to an element having a higher thermal time constant. As described above, the first sensing element may have a thermal constant of 8 second or less, 6 seconds or less, 1 second or less, 500 msec or less, or 250 msec or less.

The nature of the stimulus or interrogation pulse of energy, from an electrical standpoint, may be a step function or a controlled ramp or curve from one level to another and (optionally) back again in either direction applied to one or more interface structures of contaminant sensing elements hereof in one or more circuits simultaneously. The purpose of the pulse or brief energy change is to cause the changes in the thermodynamic properties of the interface system (arising from mass changes associated with contamination) to be revealed as it heats or cools. Because the structure is part of sensitive electronic circuitry, for example, including a Wheatstone bridge, simulated Wheatstone bridge or other bridge/simulated bridge configuration, the electrical properties of the electronic circuitry are changed in ways that are measurably different depending on the thermodynamic response of the element(s) to the stimulus pulse. These differences can then be analyzed leading to determinations that can be made about the physical condition of the structure.

Pulse width modulation may, for example, be used to control the energy delivered to elements hereof. Pulse width modulation is a well-known control technique used to control the average power and/or energy delivered to a load. In embodiments hereof, a voltage is supplied to heat an element to a desired temperature. Because the elements hereof may have relatively low thermal mass, the cycle times can be relatively short.

In pulse width modulation, heating energy (that is, heating voltage(s) or heating currents(s)) may be periodically supplied to the heating element(s) during an "ON time". Rest energy (that is, rest voltage(s) or rest current(s)), which is less than the heating energy may be supplied during a "REST time". The total of the higher-energy or ON time plus the lower-energy or REST time correspond to a cycle time or a cycle duration. Gas concentration or the analyte is measured during the ON time. The heating energy (voltages/currents) supplied during the ON time may be constant during the ON time or may be varied (for example, supplied as heating voltage/current plateau or as heating voltage/current ramp). The rest energy (voltages/currents) may be equal to zero, or be sufficiently lower than the heating energy so that the gas sensor does not consume any gas or substantially any gas to be detected. Similar to the ON time, the rest energy supplied during the REST time may be constant during all the REST time or may be varied (for example, supplied as rest voltage/current plateau or as rest voltage/current ramp). The cycle may be repeated.

An advantage to operating in pulse mode is significantly lower power consumption as compared to a continuously powered mode. Another advantage is improved span response as a result of adsorption of excess combustible gas on the catalyst at cooler temperatures during unpowered or lower powered operation (that is, during the REST time) as compared to continuously powering the catalyst at the run temperature of, for example, 350-600° C.

Figure 4A:
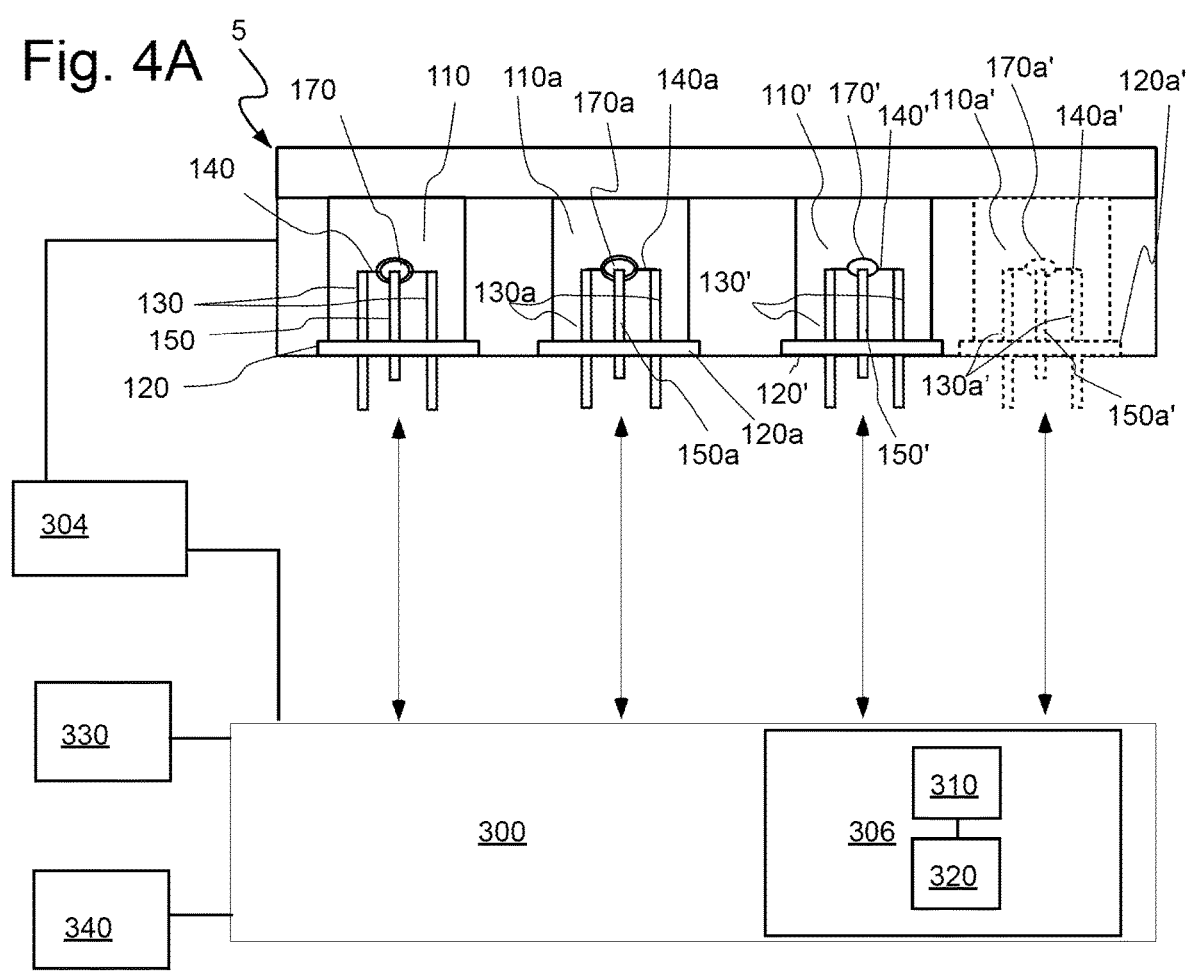
FIG. 4A illustrates schematically a combustible gas sensor device or instrument including two detector or sensor assemblies as illustrated in FIGS. 2A through 2C for analyte detection and a third, separate detector or sensor assembly of FIGS. 2A through 2C for contaminant detection in electrical connection with control and measurement circuitry.

FIG. 4A sets forth a schematic illustration of a representative embodiment of a system hereof. In the embodiment of FIG. 4A, a sensor device, instrument or system 5 includes one or two elements or element/detector assemblies 110 (a first element/pelement, as described in connection with FIGS. 2A through 2C) and 110a (a second element/pelement as described in connection with FIGS. 2A through 2C) to form a combustible gas sensor. In FIG. 4A, components of second element 110a are numbered similarly to like components of first element 110, with addition of the designation "a" thereto). First element 110 and second element 110a may, for example, be incorporated within or connected to electronic circuitry 300 (for example, via or as part of a Wheatstone bridge) to measure a concentration of an analyte. In a number of embodiments, at any time, one of elements 110 and 110a operates as an analyte element and the other of elements 110 and 110a operates as a compensating element. In a number of embodiments, each of elements 110 and 110a may include an active catalyst layer and can be alternated in function as analyte sensing element via temperature control thereof as disclosed in, for example, U.S. Pat. No. 8,826,721. The function of analyte element (high power/high temperature operation) and compensating element (for example, low power/low temperature operation) may, for example, be switched between elements 110 and 110a on a periodic basis. In other embodiments, one of elements 110 and 110a includes an active catalyst layer, while the other of elements 110 and 110a includes no catalyst or a deactivated catalyst. A dedicated compensating element may include a deactivation layer (for example, a poison layer) which destroys activity thereof to oxidize combustible gas analytes. In such a case, the one of elements 110 and 110a including the active catalyst is always operated as an analyte element, while the other of elements 110 and 110a is always operated as a compensating element.

A separate contaminant sensor is provided which includes third, separate element, a contaminant sensing element 110'. Contaminant sensing element 110' is, in a number of manners, fabricated similarly to element/detector assembly 110, and components of contaminant sensing element 110' are numbered similarly to like components of first element 110, with addition of the designation "'" thereto. Contaminant sensing element 110' may, for example, include a catalyst layer, an inactivated catalyst layer, or other inactivating layer (as known in the art for compensating elements), but need not. Interface structure 170' need only be functional or operation to adsorb contaminant thereon and undergo measurable changes in thermodynamic response properties as a result thereof. A compensating element for contaminant sensing element 110' may be provided. In a number of embodiments, second element 110a may, for example, operate as a compensating element for contaminant sensing element 110' and compensation for first element 110 may be accomplished by a temperature transducer (not shown). Second element 110a may, alternatively, provide compensation for each of first element 110 and contaminant sensing element 110'. Optionally, a separate compensating element 110a' (illustrated in dashed lines in FIG. 4A) may be provided for contaminant sensing element 110', while second element 110a functions only to compensate for first element 110. Compensating element 110a' may, for example, be matched in manufacture to contaminant sensing element 110' but may be substantially inactivated to mass deposition as further described below. Components of compensating element 110a' are numbered similarly to like components of contaminant sensing element 110', with addition of the designation "a'" thereto.

Figure 4B:
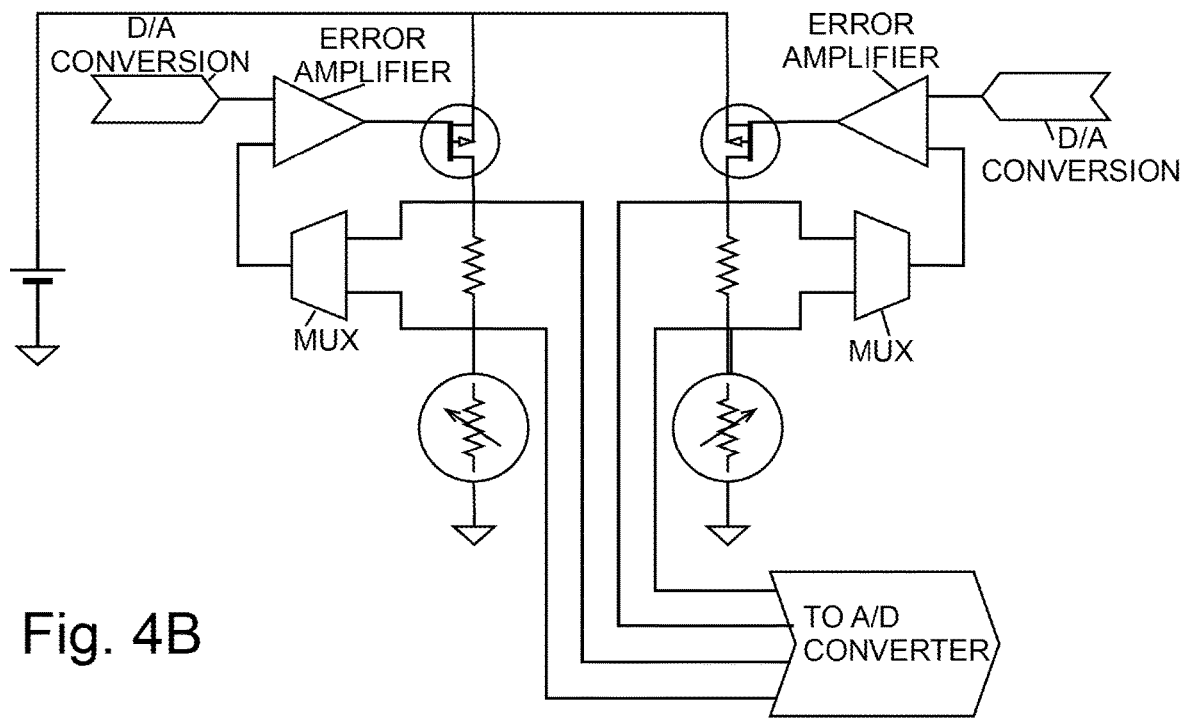
FIG. 4B illustrates an embodiment of a simulated bridge circuit for use in the circuitry of the sensor of FIG. 4A.

Electronic circuitry 300 may be, for example, placed in electrical connection with contact posts 130, 130a and 130' of each of assemblies 110 via a printed circuit board or PCB (not shown in FIG. 4A). A power source 304 provides power to electronic circuitry 300. In the case of a sensor fixed at a position within a facility, power may be provided from a remote source. In the case of a portable sensor, power source 304 may include one or more batteries. Electronic circuitry of sensor system 5 may also include a control system 306 which may, for example, include control circuitry and/or one or more processors 310 (for example, a microprocessor) and an associated memory system 320 in communicative connection with processor(s) 310. A user interface 330 (including, for example, audible, visual (for example, via a display) or tactile information transmission) to provide information to a user and via which a user may input information (for example, via a keyboard, touchscreen or other input device) and a communication system 340 (for example, including a wired and/or wireless data transceiver for remote information/data transmission) may also be provided. FIG. 4B illustrates an embodiment of a simulated Wheatstone bridge circuit incorporating contaminant sensing element 110' and compensating element 110a' which forms a part or portion of circuitry 300.

In a number of studies, contaminant sensing element 110' was formed using the same manufacturing methodologies as that of catalytically active analyte detecting/sensing element to include a catalyst supported on interface structure 170. However, contaminant sensing element 110' as incorporated and operated in the system of FIGS. 4A and 4B was inoperable to determine a concentration of a combustible gas analyte. Interface structure 170' and interface structure 170a' were formed of a refractory composition including aluminum oxide. Interface structure 170' was impregnated with a noble metal catalyst. In a number of representative studies, it was found that dynamic diagnostics on the contaminant sensor including contaminant sensing element 110' and compensating element 110a', when operated at a step voltage of 1.85 V, showed a change in response, compared to the uncontaminated state, at a heating time of 200 ms into a step of −0.87 mV±0.62 mV (mean±standard deviation) for a dose of 44 ppm-hours hexamethyldisiloxane (HMDS). Alternately, the heating curves can be fit to splines, as known in the curve fitting arts, which can predict HMDS dose with an $R^2$ of 0.91. Additional or alternative data analytical methods known to those skilled in the art such as, for example, area under the heating curves, may be used to predict HMDS dose.

In representative embodiments, a voltage step change of, for example, 2.5 seconds on, 10 seconds off, may be repeated several times and a later pulse (for example, the second pulse, the third pulse or a later pulse) is used for contaminant diagnosis. The third pulse was used in a number of embodiments hereof. In a number of studies, the period of time between contaminant exposure and dynamic diagnosis yielded similar correlations for time periods between 1 and 15 minutes.

Figure 5A:
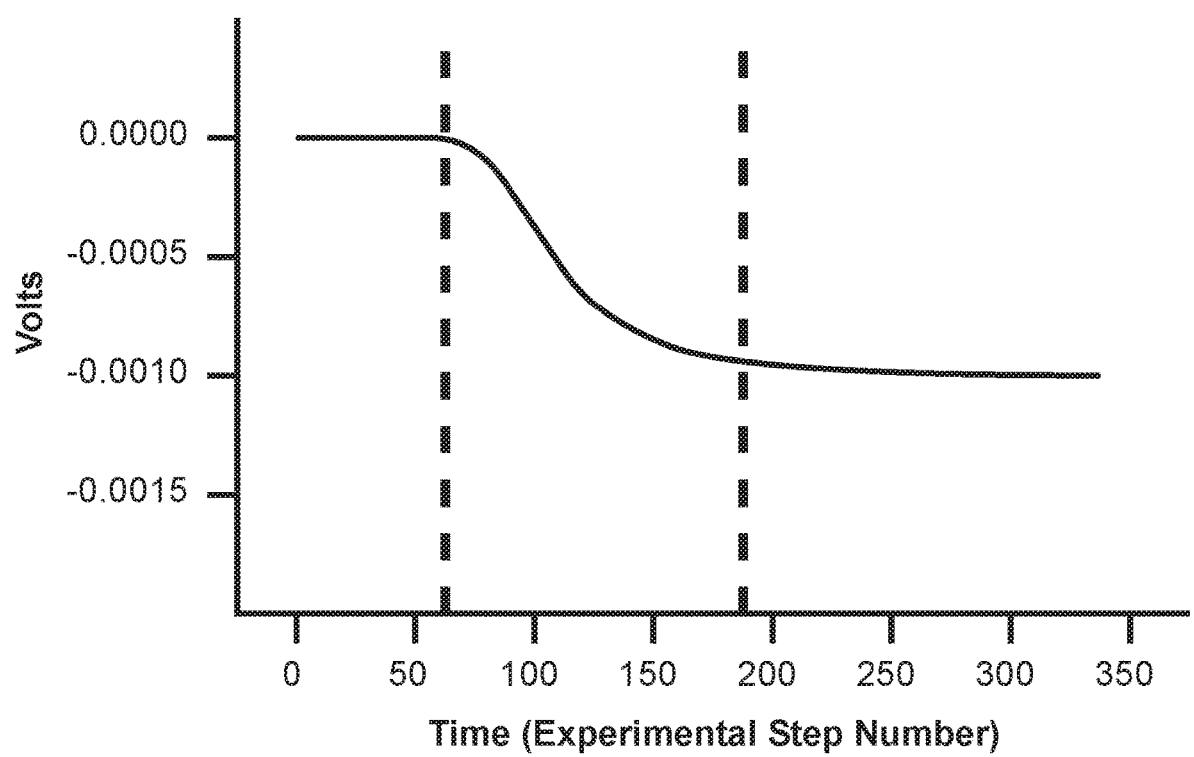
FIG. 5A illustrates change in the 200 ms dynamic response over the course of 44 ppm-h HMDS poisoning.
Figure 5B:
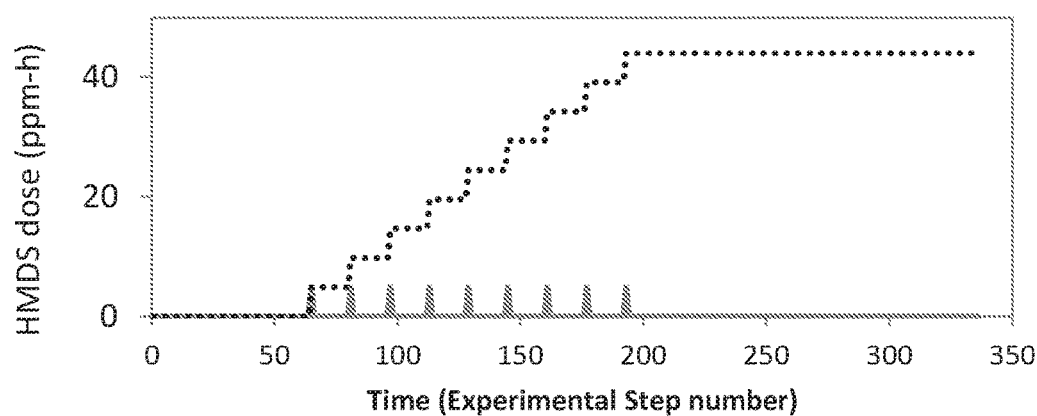
FIG. 5B illustrates the contaminant schedule for the experiment of FIG. 5A wherein the per step dose is shown by the solid line and the cumulative dose is shown by the dotted line.
Figure 6:
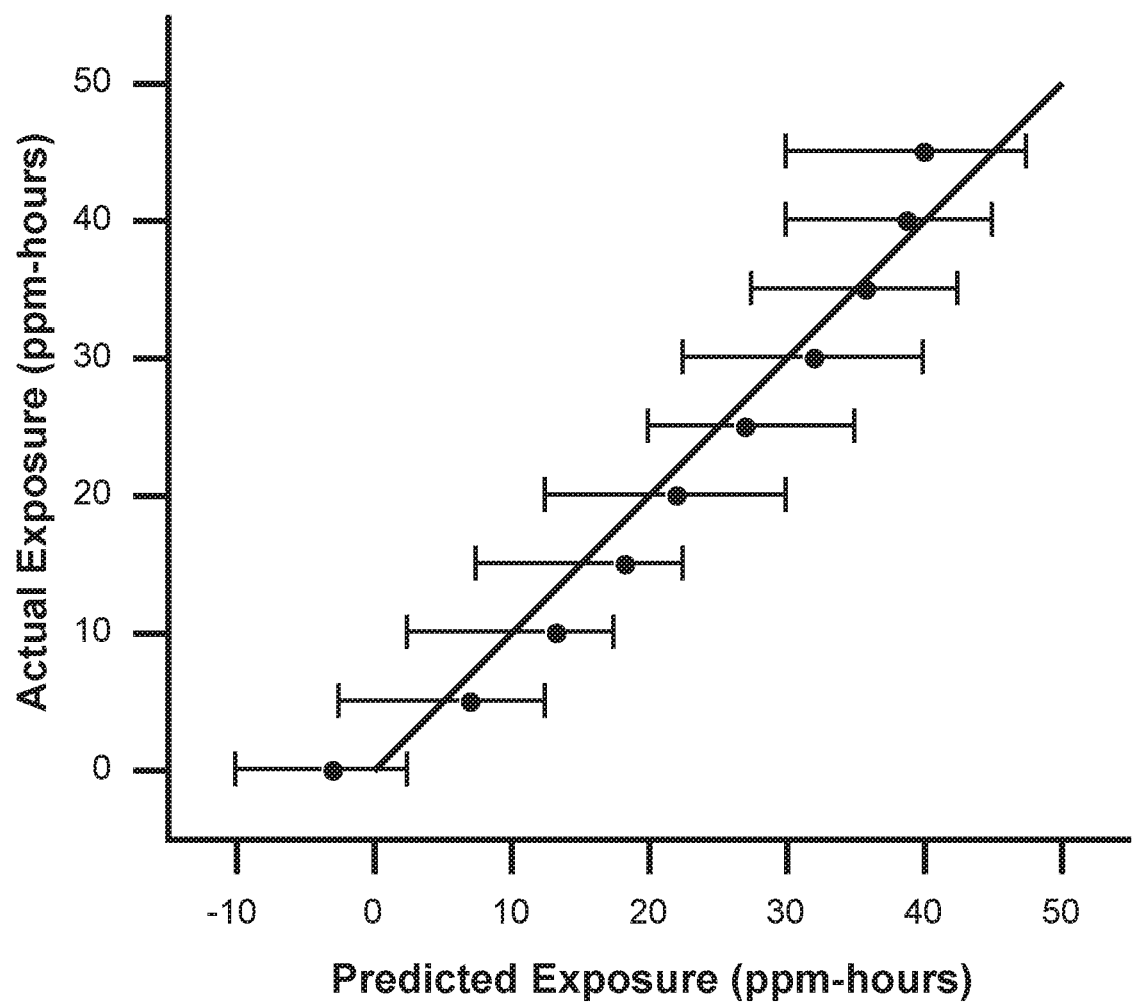
FIG. 6 illustrates predicted HMDS exposure using a balanced model with spline coefficient fits, with actual measured exposure shown on the ordinate.

In a number of studies, the material composition of contaminant sensing element 110' was varied by excluding noble metals catalysts from interface structure 170'. Further, unlike the case of compensating elements, no catalyst inactivating treatments were applied to the refractory aluminum oxide of interface structure 170' of contaminant sensing element 110' hereof. Interface structure 170a' likewise included a refractory aluminum oxide and no metal catalyst and was substantially inactivated to mass deposition of contaminants as described below. Contaminant sensing element 110' in such studies thus included (or consisted essentially of, or consisted of) heating element or component 140' (including helical coil section 142') covered in metal-oxide, ceramic interface structure 170'. In a number of embodiments, of a metal-oxide, ceramic interface structure 170' was formed of high surface area aluminum oxide. It was found that dynamic diagnostics on an oxide-only interface structure 170' of contaminant sensing element 110', when operated at a step voltage of 1.85 V, showed a change in response, compared to the uncontaminated state, at a heating time of 200 ms into a step of −0.96 mV±0.25 mV for a dose of 44 ppm-hours HMDS. Data for such studies are set forth in FIGS. 5A and 5B. Alternately, the heating curves may be fit to splines which can predict HMDS dose with an $R^2$ of 0.94, as illustrated in FIG. 6. As described above, additional or alternative data analytical methods known to those skilled in the art such as, for example, area under the heating curves, can be used to predict HMDS dose.

As also described above, a voltage step change of, for example, 2.5 seconds on, 10 seconds off, may be repeated several times and a later (for example, the second, the third or a later pulse) may be used for contaminant level diagnosis. Once again, the third pulse was used in a number of studies hereof. The time between poison exposure and dynamic diagnosis yielded similar correlations for times between 1 and 15 minutes. Lower power operation was investigated by lowering the voltage setpoint on oxide-only contaminant sensing elements 110'. Lower power operation (achieved, for example, by lowering the voltage setpoint on the elements) is possible to conserve energy. The operational power was not optimized in the experimental studies of the systems hereof, but such optimization is readily achievable for a particular system using known engineering principles. An oxide-only contaminant sensing element 110' (that is, without a metal catalyst supported thereof) was selected for further study because of its superior statistical predictive power as compared to use of a standardly produced catalytic analyte sensing element (including a supported noble metal catalyst) as contaminant sensing element 110'.

To ameliorate the effects of environmental contaminants or poisons, manufacturers of catalytic combustible sensors often incorporate filtration material(s) upstream of the catalytically active element(s) to trap the contaminating compounds. Such filters may, for example, function on physiochemical processes such as physisorption, chemisorption, chemical reaction, or a combination thereof to increase the span stability and lifetime of the combustible gas sensor. Filters for combustible gas sensors may, for example, include a variety of metal salts, activated carbon, adsorbent metal oxides or combinations thereof which have been found to reduce the effective concentration of contaminants reaching the catalytically active analyte (sensing) element. Representative examples of such filters are, for example, disclosed in United States Patent Application Publication No. 2018/0353885 and U.S. Pat. No. 6,756,016, the disclosures of which are incorporated herein by reference. Upstream filtration is not limited to separate or external filters. In that regard, filter materials may be coated directly onto the catalyst-supporting surface of support structures such as supports structure 170.

A consequence of including upstream filtration in combustible gas sensors is that sensitivity and response time can be reduced for combustible gas analytes of interest. A reduction in sensitivity or response time may be especially troublesome for heavy hydrocarbons when filters including adsorbents with high surface area (for example, greater than 75 $m^2/g$) or relatively thick filters are used.

The contaminant sensing elements hereof differ from contaminant detection or sensing structures/elements in previous combustible gas sensor systems in that the contaminant sensing element hereof are physically separate from the analyte sensing element and any compensating element. The contaminant sensing elements hereof may thus operate in a physically different location/environment than the analyte sensing element (as well as the compensating element) within the devices and systems hereof. In a number of embodiments of devices, systems and methods hereof, the separate contaminant sensing element(s) experience a different (for example, a lesser) degree of adsorbent filtration than does the analyte sensing element(s). A significant advantage is provided in such embodiments in that a high-magnitude contaminant response is possible when the contaminant sensing element is exposed to higher contaminant doses than the combustible gas analyte element can withstand without total loss of sensitivity.

In a number of representative embodiments, a combustible gas analyte element in the form of element/pelement 110 exhibited an initial sensitivity of 65 mV per 2.5% vol methane in air (operated in a constant voltage mode). Studies showed that upon exposure of a continuously powered analyte element to 15 ppm HMDS in air for 20 minutes without upstream adsorbent filtration, the post-contaminant sensitivity was reduced to 32 mV in 2.5% vol $CH_4$. The sensitivity (or the ratio between the output signal and the measure property, or vol % in this case) was thus reduced to approximately one half of the original non-contaminated sensitivity. Therefore the "contamination tolerance" or "poison tolerance" of the continuously powered analyte element to its "half-life" is a 5 ppm-hour HMDS dose, wherein ppm-hour is the product of the concentration and the exposure time.

As known to those skilled in the art, the overall or effective contaminant/poison tolerance of the above analyte element can be extended beyond a device or instrument experienced dose of 5 ppm-hour HMDS by including an adsorbent material (filter) physically located between the analyte element and the environment to be tested. In a number of embodiments, such an adsorbent material may be formed as a pressed-powder filter pellet. When sensors including such an upstream filter were exposed to HDMS contaminant, the contaminant tolerance (measured as dose to half-life) was determined to be 100-200 ppm-hour HMDS for the continuously powered analyte element (in the form of pelement 110). In other words, when exposed to 15 ppm HMDS/2.5% vol methane/air, the dose required to reduce the analyte element sensitivity from 65 mV to 32 mV was 100-200 ppm-hours HMDS, or an exposure time of 6.7-13.3 hours (see FIG. 7). At lower doses, such as 50 ppm-hour HMDS, the analyte element sensitivity was observed as 52±5 mV in the same experiment. A 50 ppm-hour HMDS dose upstream of the filter thus resulted in 20% sensitivity loss to the analyte element downstream of the filter. A 50 ppm-hour HMDS exposure for an unfiltered analyte element would result in total span loss. The dose corresponding to 20% span loss on an unfiltered element is 2 ppm-hour.

In a number of embodiments hereof, the transport pathway or filter pathway (that is, the pathway between an element and the environment to be tested, which may include one or more filters or filter components) is different for an analyte element or elements and a correlated contamination sensing element. The contamination sensing element may, for example, be positioned or located so that one or more contaminant filters (such as one or more adsorbent filters suitable to filter catalyst poisons such as organosilicon compounds) which are located between the environment being tested and the analyte element is/are not between the environment being tested and the contaminant sensing element. In such embodiments, the filter capacity of the filter pathway for the analyte element is greater than the filter capacity of the filter pathway for the contaminant sensing element. In a series arrangement, the contaminant sensing element may, for example, be positioned upstream of a particular contaminant filter or filters while the analyte element is positioned downstream of the filter or filters. Alternatively, parallel pathways with different filter capacity may be used.

In the example of the filter discussed above, the contaminant sensing element would experience a dose of 50 ppm-hour HMDS, while the filtered analyte element experiences only 2 ppm-hour HMDS, resulting in a 20% sensitivity loss in the analyte element. Once again, a significant advantage provided by the devices, systems and methods hereof is the high-magnitude contaminant response possible when the separate contamination sensing element is exposed to a high dose of contaminant (for example, a 50 ppm-hours HMDS dose in the above example) compared to a low dose of contaminant (for example, the 2 ppm-hours HMDS dose in the above example) for the combustible analyte element. The combustible analyte element can withstand the low dose experienced thereby while retaining sensitivity (for example, an 80% sensitivity retention in the above example). A user may thus be alerted to contaminants in the environment while the analyte element retains sufficient sensitivity for safety alerts. In a number of embodiments, a sensor output correction algorithm can be implemented wherein the reported response of the analyte element may be increased in an amount proportional to the predicted span loss (based upon contamination sensing element output). As clear to those skilled in the art, one may calibrate the response of the contaminant sensing element to the contaminant(s) and characterize the differences in filtration or filtration capacity between the analyte and contaminant sensing to determine a contaminant dose experienced by the analyte element.

For the measured response from the contamination sensing element to be used to predict or determine the contamination dose to which the sensor and therefore the analyte element was exposed, it must sufficiently sample the environmental contamination dose and interact with the contaminant to undergo mass addition and, therefore, contaminant response. A number of sampling approaches are possible which may, for example, be varied dependent upon the operation of analyte element. It may be desirable in some embodiments to, at least partially, match the temperature control of a compensating element to the analyte element with which the compensating element is correlated. However, it is possible (for example, via processing) to correlate compensating element response to analyte element contamination when the compensating element is operated in a different temperature control scheme than the analyte element.

In one sampling approach, in which the analyte element is operated continuously at a temperature of 350-600° C., the contaminant sensing element may be operated continuously at a temperature of 350-600° C., similar to the operation of the analyte element, in between diagnostic measurements (for example, dynamic diagnostic measurements). In an alternate sampling approach, enabling lower power operation compared to a continuous mode, one may reduce the temperature and/or run time of the contaminant sensing element. Those skilled in the art recognize that a minimum temperature may be required for oxidation of certain contaminants on the interface structure of the contaminant sensing element. Many poisons and/or inhibitors are oxidized on the surface of an element (for example, on a support structure or interface structure hereof) at a certain minimum temperature, sometimes referred to as "light-off" temperature. In the representative example of siloxane vapor, oxidation of the siloxane vapor on the element occurs below the temperature required for combustible gas detection on a noble metal catalyst. HMDS is a common siloxane contaminant and has a relatively low light-off temperatures compared to methane. Specifically, the light-off temperature of HDMS is greater than 150° C. as illustrated in FIG. 8, but well below the light off temperature of hydrocarbons such as methane. Heating a contaminant sensing element hereof via Joule heating to a temperature below a light-off temperature in the case of a contaminant such as HDMS may result in desorption of the contaminant and any effect upon thermodynamic response of the element may not be measurable. Relatively quickly heating the contaminant sensing element to a temperature above the light-off temperature results in oxidation of the HDMS to a species tightly bound upon the interface structure. Another contaminant, with a different physiochemistry, may become sufficiently bound to the interface structure to affect the thermodynamic response thereof without oxidation or other reaction on the surface of the interface structure. However, sufficient energy for Joule heating is required to effect a change in the temperature of a contamination sensing element hereof so that changes in the thermodynamic response of the contamination sensing element may be detected. In general, any composition that deposits upon the interface structure of a contaminant sensing element hereof to increase the mass thereof in the Joule heating temperature range can be detected. Such compositions include, but are not limited to sulfur compounds, silicon/organosilicon compounds, lead compounds, organophosphate compounds and halogenated compounds. For example, in a number of representative studies, it was found that dynamic diagnostics on contaminant sensing element 110', when operated at a step voltage of 1.85 V, showed a change in response at a heating time of 150 milliseconds (ms) into a step of −0.17 mV for a dose of 6 ppm-h hydrogen sulfide.

In the case of a contaminant sensor hereof for use in detecting sulfur-containing compounds, one or more sulfur active chemisorption compositions such as, for example, tin oxide, zinc oxide, copper oxide, and combinations thereof, may be used to enhance sensitivity of the contaminant sensor to deposition of sulfur-containing compound (for example, $H_2S$). Such contaminant-specific compositions may be added to sensing element 110' or sensing element interface structure 170'. As clear to those skilled in the art, other surface chemistries or compositions may be used to facilitate mass deposition (for example, adsorption/chemisorption) of other contaminant compositions.

Figure 9:
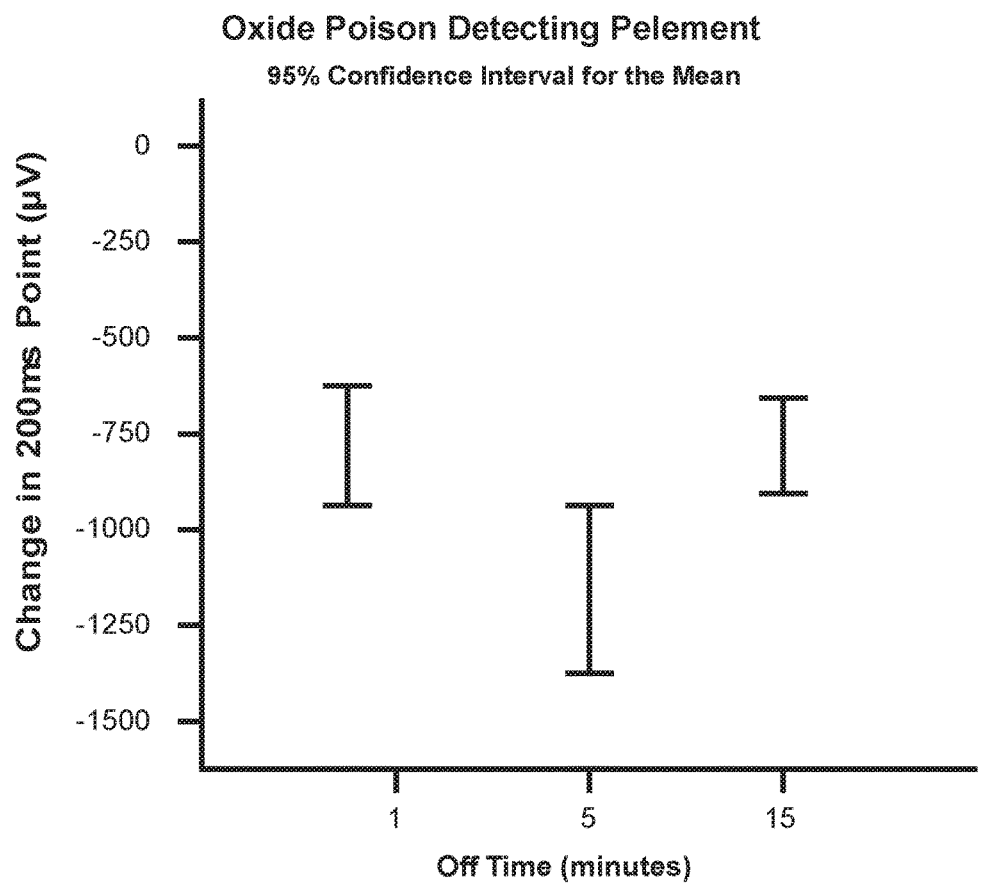
FIG. 9 illustrates response of a contaminant sensing element including an oxide interface structure to 50 ppm-hour HMDS as a function of a period of time the contaminant sensing element remains unpowered prior to application of a "loading pulse" thereto in the form of a pulse of energy.

With respect to run time of contaminant sensing elements hereof, studies of devices and systems hereof have shown that sampling the sensor vapor environment for virulent contaminants with the contaminant sensing element at a very low power over the course of 1-15 minutes is a sufficient temperature cycling rate (as, for example, illustrated in FIG. 9). Without limitation to any mechanism, it is hypothesized that cool operation of the contaminant sensing element, wherein contamination sensing element is operated at very low power, allows adsorption sites (such as oxide sites) of the interface structure of the contaminant sensing element to collect the contaminant under favorable adsorption properties (that is, at cool conditions). Under such cool conditions, the contaminant (for example HMDS) is in a condensed or adsorbed state but remains chemically unaltered. When the contaminant sensing element is subsequently heated above the light-off temperature of the contaminant (which can, for example, occur relatively quickly for an element of lower thermal mass), the contaminant available on the adsorption sites is reacted (generally oxidized in the case of silicon-containing contaminants) to a strongly held species. In the representative example of HDMS, silicon dioxide or a $Si_xC_yO_z$ species results upon heating. In a number of embodiments, the contaminant sensing element is heated to approximately 2.4 V for a single "loading pulse" with a duration of 1000 ms every 5 minutes. Approximately every four hours, the contaminant sensing element undergoes a dynamic diagnostic, which involves five pulses, preferably to 2.4 V, lasting 2500 ms each, 10 seconds apart. The power required for these two operations is about 1 mW, compared to a continuous operation power draw of 100 mW per element (pelement).

To reduce power consumption in a number of embodiments, the analyte element may be formed on a low-power MEMS hotplate sensor. MEMS sensor elements or pellistors (as described in connection with FIGS. 2A and 2B) generally have lower thermal mass than low-thermal-mass pelements (as described in connation with FIGS. 2A through 2C). As described above, conventional catalytic combustible gas sensor or detectors (for example, those including relatively large thermal mass pelements) are operated in a Wheatstone bridge circuit in constant current, constant voltage or constant resistance modes, in which the pelements are powered to run in a 350-600° C. range whenever the sensor is operational. That operational mode can be termed a "continuous" mode. In an alternative mode, particularly suitable for low-thermal-mass elements (for example, low-thermal-mass pelements or MEMS hotplates), one may quickly heat and cool the element(s) in a reduced power mode. For example, a MEMS hotplate may be powered for 1 second, then unpowered for 9 seconds, which can be referred to as operation at 10 second, 10% duty cycle. An obvious advantage to running in reduced power mode is significantly lower power consumption compared to a continuous mode. Another advantage to operation in such a reduced power mode is improved span response resulting from adsorption of excess combustible gas on the catalyst at cooler temperatures (during unpowered or low-powered, and thus low-temperature operation) compared to continuously powering the catalytically active analyte element at the run temperature of 350-600° C. In a number of embodiments, the MEMS hotplate is powered on 0.35 seconds then unpowered for 3.65 seconds for operation at a 4 second, 8.75% duty cycle. The power consumption of a MEMS hotplate operated in that manner is approximately 15 mW. Previously available, continuously operated MEMS hotplates consume approximately 100 mW.

In a number of embodiments, a MEMS hotplate including an analyte element is positioned such that an adsorbent filter is between the environment to be tested and the MEMS hotplate. The separate contaminant sensing element may be incorporated or positioned within the system so that no absorbent filter is present between the environment to be tested and the contaminant sensing element. For example, an absorbent filter can be positioned intermediate or between the MEMS hotplate and the contaminant sensing element so that the MEMS hotplate is downstream from the absorbent filter and the contaminant sensing element is upstream of the absorbent filter. The absorbent filter may, for example, be designed to have a capacity so that the contaminant sensing element has appreciable signal at a contaminant sensitivity that correlates with the analyte sensing MEMS hotplate retaining sufficient analyte sensitivity for safety alerts. In a number of embodiments, an output correction algorithm may be applied wherein the reported response from the analyte element may be increased proportional to the predicted span loss (determined, at least in part, on the basis of the contamination level measured by the contamination sensing element and the effect of the adsorbent filter pathway of the analyte element in reducing the contaminant dose experienced by the analyte element).

Figure 10A:
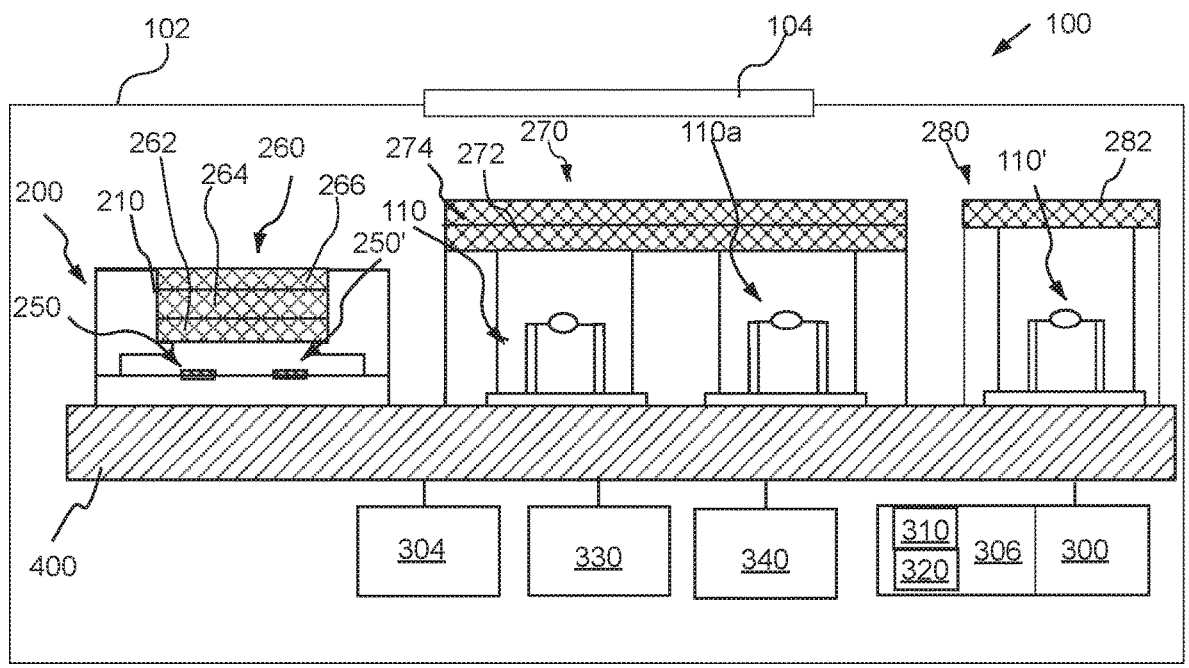
FIG. 10A illustrates schematically a combustible gas sensor device or instrument including a MEMS hotplate sensor as illustrated in FIGS. 3A and 3B which is operable as a "sniffer sensor", two low-thermal-mass pelements as illustrated in FIGS. 2A through 2C which are operable as a primary combustible gas sensor, and a third, separate low-thermal-mass pelement as illustrated FIGS. 2A through 2C which is operable for contaminant detection, all of which are in electrical connection with control and measurement circuitry via a printed circuit board or PCB 400.
Figure 10B:
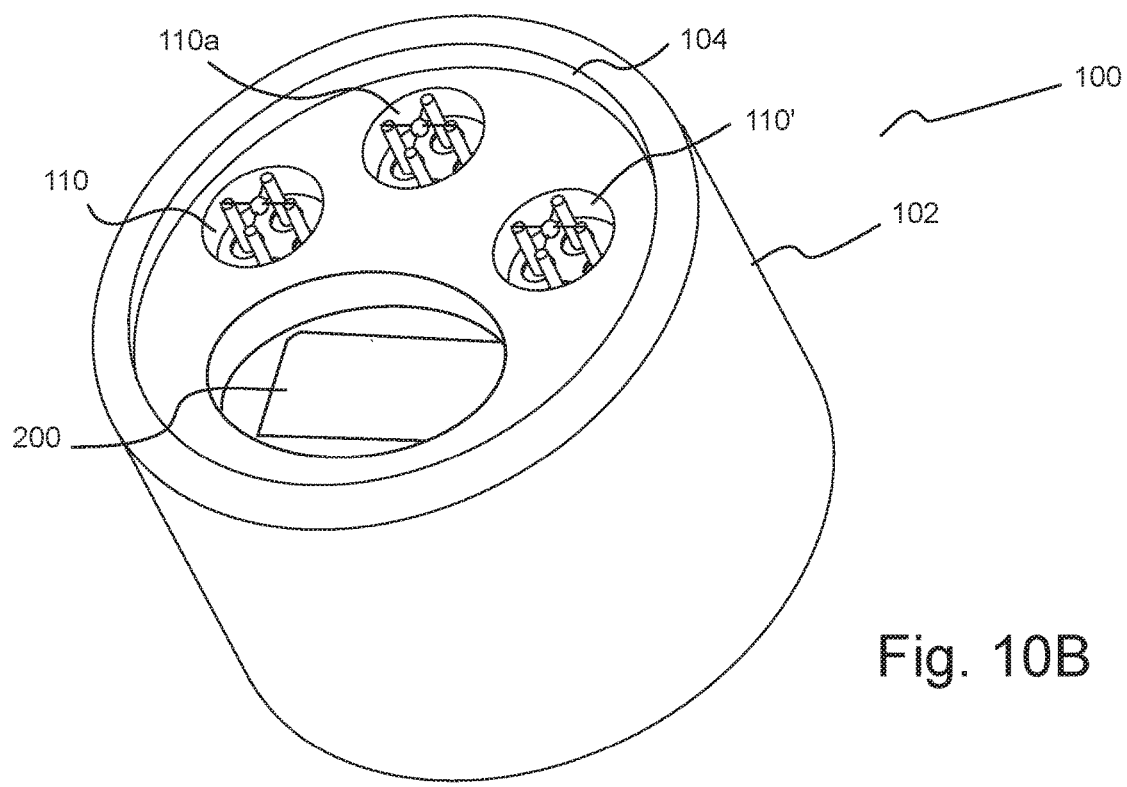
FIG. 10B illustrates a perspective view of a portion of the device or instrument of FIG. 10A without filters in place.

In a number of embodiments, a primary combustible gas sensor (such as a combustible gas sensor including helical coil-formed elements such as pelements 110 and 110a) and a trigger sensor (such as a MEMS hotplate sensor 200) may be combined into a single device, system or instrument 100 as, for example, illustrated in FIGS. 10A and 10B. In general, a lower-powered trigger sensor is used to activate a higher-powered, primary combustible gas sensor which includes one or more elements having higher thermal mass than the one or more elements of the trigger sensor. Low power MEMS hotplate sensor 200 may, for example, operate regularly at, for example, an 8.75% duty cycle. Higher power pelements 110 and 110a (which are combined in operation to form the primary combustible gas sensor) may, for example, run in a very low power "standby" state in the absence of combustible gases. Once sensor device 100 is exposed to a combustible gas environment, the analyte is detected by MEMS hotplate (trigger) sensor 200, which subsequently "triggers" higher power analyte pelements 110 and 110a to power up to an operating temperature (for example, in continuous mode). Triggered operation of a primary combustible gas sensor is, for example, described in U.S. patent application Ser. No. 16/037,882, the disclosure of which is incorporated herein by reference. Triggered operation of higher powered pelements 110 and 110a (the primary combustible gas sensor), as compared to analyte sensing solely with MEMS hotplate sensor 200, provides improved linearity and stability via the higher mass analyte pelements. In a number of embodiments, a trigger sensor with a single, low-thermal-mass element may be used. In a number of embodiments, when triggered, analyte sensing pelement 110/110a operates in a constant resistance mode, which provides better stability over temperature and better analyte sensitivity compared to other operating modes.

As, for example, illustrated in FIG. 10A, MEMS hotplate 200, each of analyte sensing/compensating pelements 110 and 110a, and contaminant sensing element 110' may be placed in connection with electronic circuitry 300 via a PCB 400. Because system 100 includes at least one containment sensing element 110', which is separate from all analyte detection or sensing elements, separate filter pathways (with different filtration characteristics) may be designed therefor. As illustrates in FIGS. 10A and 10B, a matched compensating element for contaminant sensing element 110' may be absent. Temperature compensation for contaminant sensing element 110' may, for example, be accomplished by a temperature transducer (not shown), by compensating element 110a, or by a combination of the two. As, for example, schematically illustrated in FIG. 10A, a first filter pathway 260 is present between elements 250 and 250' of MEMS hotplate (trigger) sensor 200 and an inlet 104 in housing 102 of device 100, a second filter pathway 270 is present between pelements 110 and 110a and inlet 104, and a third filter pathway 280 is present between contaminant sensing element 110' and inlet 104. Each of filter pathways 260, 270 and 280 may include one or more separate filter components and/or one or more filter components may be shared between different filter pathways. In FIG. 10A, filter pathway 260 includes a first sorbent filter 262, a second sorbent filter 264 and a sulfur filter 266, filter pathway 270 includes a first sorbent filter 272 and a sulfur filter 274, and filter pathway 280 includes only a sulfur filter 282.

Figure 11:
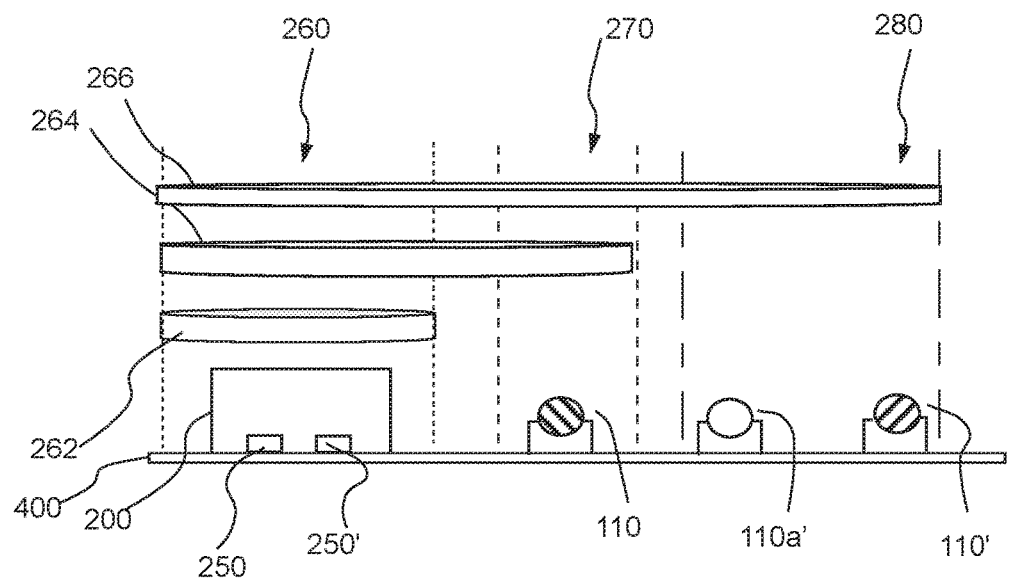
FIG. 11 illustrates schematically another embodiment of a combustible gas sensor device or instrument including a MEMS hotplate sensor which is operable as a "sniffer sensor", a pelement assembly as illustrated in FIGS. 2A through 2C which is operable as a triggerable primary combustible gas sensor, two separate pelement assemblies as illustrated in FIGS. 2A through 2C which are operable as a contaminant sensor, all of which are electrical connection with control and measurement circuitry via a PCB 400.

In the embodiment of FIG. 11, sorbent filter 262 is present only in filter pathway 260, while sorbent filter 264 is shared between filter pathways 260 and 270, and sulfur filter 266 is shared between filter pathways 260, 270 and 280. Referring to, for example, FIG. 11, one homogeneous sorbent pellet 264 may or may not be located upstream (that is, between an environment to be tested and the element) of analyte element 110 and MEMS hotplate elements 250 and 250' (that is, within filter pathways 260 and 270). Another homogeneous sorbent pellet 262, which may be formed with the same material(s) of sorbent pellet 264, is located upstream of only MEMS hotplate 200 (that is, in filter pathway 270 only). In the embodiment of FIG. 11, sulfur filter 266 is located upstream of each of MEMS hotplate sensor element 250 and 250', analyte element/element 110, and contaminant sensing element 110' (that is, within each of filter pathways 260, 270 and 280. The filter pathway designs of FIGS. 10A and 10C provide for additional adsorbent filtration (which may, for example, remove poisons such as HDMS) via filter pathway 260 as compared to filter pathway 270. The additional absorbent filtration of filter pathway 260 provides additional environmental contaminant/poison tolerance to lower-mass-elements 250 and 250' of MEMS hotplate sensor 200. On the other hand, analyte element/pelement 110 includes less sorbent filtration via filter pathway 270, which allows for faster analyte response (once triggered) compared to the more filtered MEMS hotplate sensor 200. Such multiple-filter-pathways designs may, for example, speed response to heavy hydrocarbons while still providing some contaminant filtration for analyte element 110. Further in the embodiment of FIG. 10A, filter pathway 270 is common to both elements 110 and 110a, while in the embodiment of FIG. 11, filter pathway 270 is in fluid connection with only element 110, while filter pathway 280 is in fluid connection with contaminant sensing element 110' and compensating element 110a' therefor.

In a number of embodiments, each of elements 250 and 250' of MEMS hotplate sensor 100 may or may not include an active catalyst layer and can be alternated in function as analyte sensing element via temperature control thereof as disclosed in, for example, U.S. Pat. No. 8,826,721. The function of analyte sensing element (high power/high temperature operation) and compensating element (low power/low temperature operation) may, for example, be switched between elements 250 and 250' on a periodic basis (for example, every seven days. Sensitivity correction based upon measurement of contaminant level via contaminant sensing element 110' is more complicated in the case of alternating the function of elements 250 and 250'. In such embodiments, it may, for example, be desirable to provide only safety alert based upon measure contaminant/poison exposure to avoid complexity in processing. It is also possible, that one of elements 250 and 250' includes an active catalyst layer, while the other of elements 250 and 250' includes no catalyst or a deactivated catalyst. In such a case, the one of elements 250 and 250' including the active catalyst would always be operated as an analyte sensing element while the other of elements 250 and 250' would be operated as a compensating element.

Like elements 250 and 250' of MEMS hotplate sensor 200, elements/pelements 110 and 110a, may each include an active catalyst layer and can be alternated in function as analyte sensing element via temperature control thereof. In such embodiments, the function of analyte sensing element (high power/high temperature operation) and compensating element (low power/low temperature operation) may, for example, be switched between elements/pelements 110 and 110a on a periodic basis. Alternatively, one of elements 110 and 110a may include an active catalyst layer, while the other of elements 110 and 110a includes no catalyst, a deactivated catalyst, and/or a deactivated layer. In such a case, the one of elements 110 and 110a including an active catalyst layer would always be operated as an analyte sensing element while the other of elements 110a and 110a would be operated as a compensating element.

In a number of embodiments including MEMS hotplate sensor 200 as a "sniffer" sensor to determine presence of an analyte in an environment and higher-thermal-mass pelements 110/110a, which may be triggered" by a positive response from MEMS hotplate sniffer sensor 200, the response of contamination sensor element 110' is correlated with the contaminant dose sampled by the regularly cycling MEMS hotplate sensor 200. In that regard, the MEMS hotplate sensor may be correlated with the measured contaminant dose because operation of the MEMS hotplate sensor enables the overall sensor analyte gas detection. As for the analyte pelement (such as analyte pelement 110), when it is not powered, it may not experience significant poisoning resulting from temperature activated deposition reactions. Because the analyte pelement is powered only sporadically (that is, only when triggered), additional comparative calculations would be required to determine the contaminant dose before and during operation. In that regard, only high-temperature operation might measurably load certain contaminants on the analyte detecting pelement, while incident doses during long unpowered or low-powered (that is, low-temperature) operational times should be discounted. The degree of contaminant response resolution and the computational effort required to track the analyte pelement state during contaminant dosing may add complexity to the design. Therefore, in a number of embodiments including, for example, goal of analyte sensitivity correction, the response from the contaminant sensing element may be correlated with only the MEMS hotplate sensor analyte sensing element(s).

In other embodiments, including, for example, a goal of analyte sensitivity correction, "triggered" analyte pelement 110, in, for example, the configuration of FIG. 10A through 11, may be operated in the low-power analyte sampling mode to load contaminants at the same rate as MEMS hotplate sensor and correlated contaminant sensing element 110'. Analyte pelement 110 may, for example, operated with a "loading pulse" to 2.4 V with a duration of 1000 ms every 5 minutes.

Figure 12:
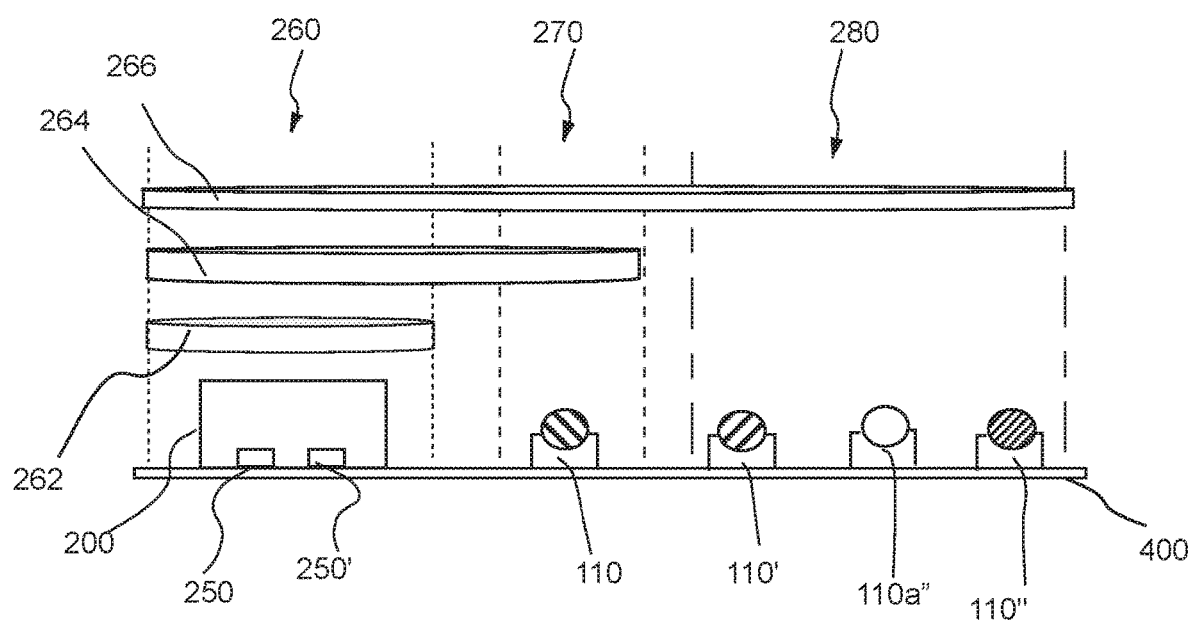
FIG. 12 illustrates schematically another embodiment of a combustible gas sensor device or instrument including a MEMS hotplate sensor as illustrated in FIGS. 3A and 3B which is operable as a "sniffer sensor", a low-thermal-mass pelement which is operable as a sensor for analyte detection, a second, separate low-thermal-mass pelement which is operable as a first contaminant sensor in connection with a third low-thermal-mass pelement used for compensation and a fourth low-thermal-mass pelement which is operable as a second contaminant sensor in connection with the third, compensating pelement, wherein the first contaminant sensor is correlated with the MEMS hotplate sensor, and the second contaminant sensor is correlated with the analyte sensing pelement(s).

In the embodiment illustrated in FIG. 12, a second contaminant sensing element 110" is included (in filter pathway 280). Second contaminant sensing element 110" may, for example, be powered to sample the tested environment for contaminants for times representative of the operation times of the triggered analyte pelement 110. Although the embodiment of FIG. 12 requires an additional element compared to the embodiments of FIGS. 10A through 11, additional contaminant sensing element 110" requires less power to operate than first contaminant sensing element 110', and, like analyte sensing element 110, may remain in a very low power state other than when analyte sensing element 110 is triggered. The response of additional or second contaminant sensing element 110" may be readily correlated with analyte pelement 110 with a goal of analyte sensitivity correction. Alternately, element 110" could consist of different materials and/or contaminant sensing regimes in order to detect a different poison than 110a".

In embodiment in which the MEMS hotplate sensor includes two catalytically active elements, the contamination sensing element may reasonably be correlated with both of the catalytically active element for embodiments including the goal of analyte sensitivity correction. In such embodiments, both MEMS elements should sample the same contaminant environment. This may be accomplished by a configuration that alternates between the element of the MEMS hotplate sensor as the high-temperature, combustible gas analyte sensing element.

Temperature compensation is required for both analyte sensing response and contaminant sensing response, since both sensors are thermal-based sensors. In a number of embodiments (see, for example, FIG. 11), combustible analyte sensor temperature compensation may be accomplished by a temperature transducer (not shown), a low-power, low-temperature MEMS hotplate element, or a combination of the two. A motivation for designing a MEMS hotplate sensor or a low-thermal mass pelement sensor with two catalytically active elements or detectors is to double the sensor life compared to one active element/detector. As discussed above, the element that is not powered as the analyte sensing element can be powered to a lower level to function as the temperature compensator as described in U.S. Pat. No. 8,826,721.

Temperature compensation for contaminant sensing elements hereof may, for example, be accomplished using a helical-wire compensator pelement 110a' which has a sensitivity to mass deposition that is substantially reduced via a chemical deactivation process as disclosed in U.S. Pat. No. 5,401,470. Compensator pelement 110a' may, for example, be operated in the same dynamic diagnostic mode as the contaminant sensing element. It was discovered that loading a compensating element for a contaminant element hereof with, for example, a silicon or organosilicon compound such as HDMS rendered the thermodynamic response of such a compensating element substantially insensitive to further mass loading from a contaminant compound. In the case of low-thermal-mass pelements as described above, a dose of approximately 25,000 ppm-h was used to lower the sensitivity or the compensating element to mass deposition of contaminants.

Because mass deposition of a siloxane compound such as HDMS is destructive to the sensitivity of contaminant elements hereof to mass deposition, a specific contaminant element cannot be readily calibrated via exposure thereof to a particular dose of HDMS. By careful manufacture of contaminant elements hereof, one contaminant element can be exposed to, for example, HDMS to determine a calibration for other, like contaminant elements which are manufactured in the same manner. Alternatively, a contaminant/composition which does not form an irreversible bond with the interface structure may be used to calibrate a specific contaminant element that may later be used in a contaminant sensor hereof. In that regard, after the calibration, the removable contaminant may be removed from the contaminant element. For example, a sulfur compound may be used to calibrate a particular contaminant element and subsequently "burned off" that contaminant element at high temperature.

Using a thermally matched temperature compensating element or compensator for determination of contaminant exposure may, for example, provide an improved signal-to-noise ratio when compared to a cool element. This may be particularly advantageous in the case of the relatively small signals generated in determining thermodynamic changes resulting from, for example, mass changes arising from dosages in relatively low ppm-hour ranges. During field operation, the temperature measured by the sensor temperature transducer may reference the appropriate bridge coefficients to obtain specified contamination detection performance. In a number of embodiments, the contaminant sensing element(s) and temperature compensation element(s)/pelement(s) therefor may be positioned in similar but separate thermal environments with the same degree of adsorbent filtration or lack thereof. In a number of embodiments, the contaminant sensing element(s)/pelement(s) and the temperature compensation element(s)/pelement(s) are located downstream of only minimal sorbent filtration, or downstream of no sorbent filtration.

In FIG. 11 compensating element 110a' operates to compensate for contaminant sensing element 110'. Compensating element 110a' may, for example, be operated under the same power scheme as contaminant sensing element 110' in the embodiment of FIG. 11. In FIG. 12 compensating element 110a" is operated to compensate for each of contaminant sensing elements 110' and 110". Compensating element 110a" may, for example, be operated under a power scheme that is a combination or overlay of the power schemes if contaminant sensing element 110' and contaminant sensing elements 110" in the embodiment of FIG. 12.

Although certain advantages may be achieved using elements having low volume/low thermal mass as described above, the devices, systems and methods described above may also be used with element of relative high volume/high thermal mass. For example, standard pelements, which may have an effective diameter of greater than or equal to 1 mm may be used herein.

In a number of embodiments, the catalytically active analyte sensing elements may function as auxiliary contaminant sensing elements. The operation of catalytically active, sensing or analyte elements to detect a deposited contaminant thereon in both comparative/continuous and dynamic diagnostic modes is disclosed in US Patent Application Publication Nos. 2018/0335412 and 2018/0335411, the disclosures of which are incorporated herein by reference. In the devices systems and methods hereof, the low level contaminant exposures measurements provided by the analyte sensing element(s) may, for example, indicate or confirm the need for a safety alert regarding contaminant penetration of a filter or filter pathway. Use of the separate contaminant sensing element (that is, a contaminant sensing element separate from any analyte sensing element) provides significantly superior contaminant response compared to use of an analyte sensing element or element to measure contamination. The improved response enables, for example, improved instrument output correction algorithms.

As described in US Patent Application Publication Nos. 2018/0335412 and 2018/0335411, an active, sensing or analyte element in a number of combustible gas sensors hereof may, for example, be operated at a generally constant voltage, a constant current or a constant resistance (and thereby at a constant temperature) during a particular mode of operation. In a number of embodiments of combustible gas sensors hereof, the electronic circuitry of the combustible gas sensor operates in a first mode in which a first or sensing element is heated to or operated at a temperature at which the first catalyst catalyzes combustion of the analyte gas (for example, above 300° C. for methane). In a second mode, the electronic circuitry operates to heat the sensing element to a second temperature which is lower than the first temperature. The second temperature is below the temperature at which the first catalyst catalyzes combustion of the analyte gas but is at or above a temperature at which Joule heating of the first element occurs. The second temperature may also be below the light off temperature of other combustible gasses that may be in the environment being tested by the sensor. The second temperature is also typically lower than a temperature at which one or more predetermined inhibitors and/or poisons which may be predetermined (for example, inhibitor(s) or poison(s) that may be present in the ambient environment) are, for example, oxidized upon or within the support structure of the first element. Once again, however, the second temperature is at or above the temperature at which Joule heating occurs so that changes in mass affect upon the thermodynamic properties of the contamination sensing element may be measured. In that regard, mass deposition on the surface of all elements hereof changes the thermodynamic response of the elements. Although the change in thermodynamic response may be measured as an electrical response in, for example, a Wheatstone bridge circuit, heating is required to observe the response.

The electronic circuitry hereof measures a variable in the second mode related to a mass of the first element. The variable is measured over time (that is, through multiple cycles between the first mode and the second mode), and change in the variable over time is analyzed to relate the change in the variable to a change in mass of the first element. The change in mass is an indication of deposition of a poison or inhibitor of the catalyst of the first element. For example, voltage, current or resistance of the second element can be measured (depending upon the manner in which the system is driven to control voltage, current and/or resistance in the second mode).

In a dynamic diagnostic scheme, the electronic circuitry is configured to apply an interrogation pulse to the analyte element in which energy to analyte first element is increased or decreased to induce an associated response from the analyte element. The electronic circuitry is also configured to analyze the associated response and to determine from the associated response if poisoning or inhibiting of the first catalyst has occurred. In that regard, one or more thresholds for changes in response or changes in values may, for example, be established which are predetermined to indicate if a change in mass of an analyte element has occurred. For example, thresholds for changes in response such as change in slope of a curve, changes in area under the curve, and/or changes in values at one or more times along the curve may be predetermined.

The shape of the response is the result of the associated electronic circuitry's (for example, a bridge's) response to the non-linear changes in the resistance of the elements. Over the duration of the energy pulse, elements are changing from one thermal state to another as described above. The elements do not necessarily change at the same rate at the same point in time during the changing thermodynamic phases of the event. The resistance in each element changes (for example, perturbing the balance of the bridge circuit) in step with the non-linear thermal changes in the heating element and the catalyst/support structure system. The resulting non-linear change in the measured variable (for example, voltage) may be referred to as an interrogation pulse which can be analyzed electronically or mathematically. In addition to various bridge and other circuits, the analyte element and compensating element may be driven separately.

Elements hereof may transition through three phases during a dynamic diagnostic energy pulse. In an energy pulse in which the element begins in a relatively low-energy state (for example, at ambient temperature or a temperature below which joule heating of the heating element occurs), the applied pulse of energy causes dynamic heating of the element. One skilled in the art will appreciate that similar information can be obtained from an element that is initially at a high temperature state (for example, an analyte element operating at a temperature at or above which catalytic combustion of an analyte occurs) and energy is removed from the element to cause dynamic cooling of the element to a lower temperature (for example, to a temperature below the temperature at which joule heating occurs or to ambient temperature). During joule or resistive heating, passage of an electric current through conductive heating element releases heat, which may be referred to as a resistive phase. During a conductive phase, heat from the heating element transfers from the heating element to the catalyst support structure and the catalyst supported thereon (conduction or conductive heating). Heat transfer then occurs via fluidic convection (convection or convective heating) through the surrounding gases. Eventually, a thermal equilibrium will be reached. Once again, thermal equilibrium will be reached and remain balanced until (a) the ambient temperature changes, or (b) the makeup of the surrounding gas mixture is altered, or (c) the transfer of heat between the wire and the mass of the element changes (as a result of a mass or density change), all of which are competing and interacting effects.

A response curve hereof may also be obtained in which energy (and correspondingly temperature) is decreased from a higher energy state to a lower energy state. In such an embodiment, an element may begin in a convective phase and transfer through a conductive phase above until thermal equilibrium is achieved as described above. The decrease in energy may, for example, be of sufficient magnitude and length such that the temperature of the element decreases to a temperature below the temperature at which Joule heating commences. Differences between the first pulse and subsequent pulses have been observed to correlate with the presence of volatile species, such as water vapor, and ambient temperature.

In the case of operation of either a contaminant sensing element or an analyte sensing element hereof to detect mass deposition of one or more contaminant compositions, additional information may be obtained by examining the response in the different phases of heating as described above. In that regard, the greatest effect from contamination may occur during the peak conductive heating phase with measurably less or no effect in the trailing convective phase. This result indicates that the interface structure or support structure underwent physical changes in its internal structures. For example, this occurs when a sulfur-containing contaminant reversibly adsorbs onto the structure. If such an adsorbate has been identified, one may attempt a higher-temperature heating period to desorb the contaminant from the element and return the element to its original sensitivity.

Additional consideration may also be given to the convective phases of the interrogation pulses. If significant displacement has occurred in the trailing convective phase it may indicate that a contaminant material is deposited (for example, oxidized) on the outside of the interface/support structure, thereby changing the convective heat transfer characteristics. As additional mass deposition occurs, the change in signal continues to progress and may be represented in many measurable forms. Such a result is observed in the case of silicon-containing compositions such as HDMS which cannot be removed via high-temperature heating. Thus, examining different regions of the response curve to a dynamic energy change may provide additional information regarding the nature of the contamination and determine future actions to be taken.

The devices, systems and methods hereof may, for example, be used in connection with other devices, systems and methodologies for detecting contamination (poisoning or inhibiting) of catalytically active analyte sensing elements (including for example, electronic interrogations methodologies which do not require application of a test or other gas to the sensor). For example, devices, systems and methods disclosed in U.S. Patent Application Publication No. 2014/0273,263, the disclosure of which is incorporated herein by reference) may be used. In such devices, systems and methods, a variable related to the complex component of impedance, which is sometimes referred to as reactance, of the first sensing element (variables that may be measured include, but are not limited to, impedance, reactance, resonant frequency, a frequency dependent variable, inductance, capacitance, or the resistive components of inductance and/or capacitance). Changes in the measured variable over time are used to determine the operational status of the analyte sensing element. Changes in a variable related to reactance are particularly sensitive to contamination of the interior structure of a catalyst support structure and may, for example, be used in conjunction with other systems and methods hereof to assist in determining the existence and nature of any contamination of an element hereof.

In a device, system or method hereof, the measured variable of contaminant sensing element hereof may be used to correct gas concentration output/readings in real-time. Below is a representative example of a formula for adjusting the sensitivity of the system.

$$S_t = S_o * (D_o / D_t * k)$$

In the above equation, $S_t$ is the sensitivity at a given time t; $S_o$ is the initial or previously determined sensitivity, $D_o$ is the initial or previously determined variable related to the dynamic interrogation mode, $D_t$ is the variable measured at a given time t and k is a scaling factor constant. A lookup table may, for example, alternatively be used to relate a change in the measured variable to a sensitivity correction.

Furthermore, one or more measured variables hereof may be used as a trigger to apply additional heat to the catalyst support structure of an analyte element to potentially remove inhibitors. Periodic measurement of the variable, analysis of the results thereof, correction of sensor output and/or application of additional heat may, for example, be effected by control system 306 (via, for example, an algorithm or algorithms stored in memory system 320 as software) in an automated manner without user intervention. The measurement of a variable (for example, voltage, current or resistance) and associated application of additional heat may be done in real time and offer not only a life and health aspect for the system, but a self-curing attribute. Moreover, if the sensor fails to "burn off" a contaminant, it can be determined that the contaminant is a poison. The user may be notified that the active element of the system has been poisoned (for example, via display system 340, alarm system of user interface system 330 and/or other user interfaces). The "burn off" procedure described herein may, for example, be used in connection with any electronic interrogation of the active sensing element that is suitable to determine that a foreign material has contaminated the active sensing element.

An electronic interrogation or control algorithm or process may be implemented as described in US Patent Application Publication Nos. 2018/0335412 and 2018/0335411. In that regard, each time a variable related or indicative to mass change in a contaminant sensing element is measured, it is evaluated. If the variable and/or a correction of analyte element sensitivity associated therewith is within normal limits (for example, +/−1% of a predetermined or threshold value), no corrections occur and the sequence repeats. If a non-conforming result is obtained (that is, the variable and/or correction is not within normal limits), different actions are taken depending upon whether sensitivity should be increased or decreased, which is dependent upon the measured variable. If the measured variable results in a need to increase the sensitivity (for example, associated with contamination of the sensing element), the algorithm will determine if the increase is within normal limits, and do so. If the increase is within normal limits, the system will attempt to increase the heat to burn off any inhibitors, and the user may, for example, be alerted that this "burn-off" or cleaning process is taking place. If the maximum thermal limit has already been applied, and the maximum correction has also been applied, then the user may, for example, be alerted that the analyte element has been poisoned. If the measured variable results in the need to decrease the sensitivity, the algorithm will determine if the decrease is within normal limits, and do so. If the decrease is within normal limits, the system will check to see if heat had been previously applied to attempt to burn off an inhibitor. If heat had been applied, the heat will be reduced. This control algorithm or a similar algorithm hereof may, for example, be an automated procedure carried out via control system 306 without the need for user intervention. The control algorithm may, for example, be embodied in software stored within memory system 320 and executed by processor(s) 310 of control system 306. The combustible gas sensor hereof may be operative to detect the combustible gas analyte during the execution of the electronic interrogation, control algorithm or process.

The devices, systems and/or methods described herein can be used in connection with a variety of types of combustible gas sensors. Existing combustible gas sensors designs are readily modified to include a device or system hereof for measuring a variable related to mass change of one or more sensing elements thereof. For example, such devices, systems and/or methods can be used in connection with Micro-Electro-Mechanical Systems (MEMS), thin/thick film system, or other suitable micro- or nanotechnology systems such as, for example, described in U.S. Pat. Nos. 5,599,584 and/or 6,705,152, as well as metal oxide semiconductor (MOS) sensors (such as $H_2S$-MOS sensors and solid state $O_2$-MOS sensors).

The foregoing description and accompanying drawings set forth embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A system for detecting an analyte gas in an environment, comprising:
   a first combustible gas sensor, comprising a first element which comprises a first electrically conductive heating element, a first support structure on the first electrically conductive heating element and a first catalyst supported on the first support structure,
   a first contaminant sensor separate and spaced from the first combustible gas sensor, the first contaminant sensor comprising a first contaminant sensor element which comprises a first electrically conductive heating component and a first interface structure on the first electrically conductive heating component, the first contaminant sensor further comprising a second contaminant sensor element, the second contaminant sensor element comprising a second electrically conductive heating component and a second interface structure on the second electrically conductive heating component, and
   and electronic circuitry in electrical connection with the first combustible gas sensor and in electrical connection with the first contaminant sensor, the electronic circuitry being configured (1) to provide energy to the first electrically conductive heating element to heat the first element to at least a first temperature at which the first catalyst catalyzes combustion of the analyte gas, (2) to determine if the analyte gas is present based on a response of the first combustible gas sensor while the first element is heated to at least the first temperature (3) to provide energy to the first electrically conductive heating component, (4) to operate the second contaminant sensor element as a compensating element for at least the first contaminant sensor element to compensate for ambient conditions, and (5) to measure a response of the first contaminant sensor over time, wherein the measured response of the first contaminant sensor is a thermodynamic response which varies with mass of one or more contaminants to which the system has been exposed in the environment over time and which are deposited on the first interface structure of the first contaminant sensor.

2. The system of claim 1 wherein the second contaminant sensor element is treated to be generally insensitive to at least one of the one or more contaminants.

3. The system of claim 2 wherein the second contaminant sensor element is treated with a predetermined amount of an oxidized organosilicon compound.

4. The system of claim 1 wherein the first interface structure is selected to adsorb at least one of the one or more contaminants that undergo oxidation upon heating.

5. The system of claim 1 wherein the first interface structure comprises an oxide.

6. The system of claim 5 wherein the first interface structure has a surface area of at least 75 $m^2/g$.

7. The system of claim 1 wherein the first contaminant sensor element comprises no metal catalyst.

8. The system of claim 1 wherein the first contaminant sensor element consists essentially of the first electrically conductive heating component and the first interface structure, which consists essentially of an oxide.

9. The system of claim 1 further comprising a first filter pathway between the first combustible gas sensor and the environment, the first filter pathway having a first capacity to remove at least one of the one or more contaminants, and a second filter pathway between the first contaminant sensor and the environment, the second filter pathway have a second capacity to remove at least one of the one or more contaminants, wherein the second capacity is less than the first capacity.

10. The system of claim 9 wherein the first capacity comprise a first adsorbent filtration capacity and the second capacity comprises a second adsorbent filtration capacity, less than the first adsorbent filtration capacity.

11. The system of claim 1 further comprising a first filter pathway between the first element of the first combustible gas sensor and the environment, the first filter pathway having a first capacity to remove at least one of the one or more contaminants, and a second filter pathway between the first contaminant sensor element and the environment, the second filter pathway have a second capacity to remove at least one of the one or more contaminants, wherein the second capacity is less than the first capacity.

12. The system of claim 11 wherein the first capacity comprise a first adsorbent filtration capacity and the second capacity comprises a second adsorbent filtration capacity, less than the first adsorbent filtration capacity.

13. The system of claim 12 wherein the second adsorbent filtration capacity is zero.

14. The system of claim 11 wherein the first contaminant sensor element is low-thermal mass element.

15. The system of claim 14 wherein the first contaminant sensor element has a thermal time constant less than 8 seconds.

16. The system of claim 1 wherein a pulse is applied to the first contaminant sensor element in which energy to the first contaminant sensor element is increased or decreased to induce the measured response from the first contaminant sensor element, the electronic circuitry being configured to analyze the measured response.

17. The system of claim 16 wherein the electronic circuitry is configured to apply a plurality of pulses to the first contaminant sensor element over time in which energy to the first element is increased or decreased to induce the measured response from the first contaminant sensor element in each of the plurality of pulses, the electronic circuitry being configured to analyze one or more of the measured responses.

18. A method for detecting an analyte gas in an environment, comprising:
   providing a first combustible gas sensor, the first combustible gas sensor comprising a first element which comprises a first electrically conductive heating element, a first support structure on the first electrically conductive heating element and a first catalyst supported on the first support structure,
   providing a first contaminant sensor separate and spaced from the first combustible gas sensor, the first contaminant sensor comprising a first contaminant sensor element which comprises a first electrically conductive heating component and a first interface structure on the first electrically conductive heating component, the first contaminant sensor further comprising a second contaminant sensor element, the second contaminant sensor element comprising a second electrically conductive heating component and a second interface structure on the second electrically conductive heating component, providing electronic circuitry in electrical connection with the first combustible gas sensor and with the first contaminant sensor, and
   operating the electronic circuitry (1) to provide energy to the first electrically conductive heating element to heat the first element to at least a first temperature at which the first catalyst catalyzes combustion of the analyte gas, (2) to determine if the analyte gas is present based on a response of the first combustible gas sensor while the first element is heated to at least the first temperature (3) to provide energy to the first electrically conductive heating component, (4) to operate the second contaminant sensor element as a compensating element for at least the first contaminant sensor element to compensate for ambient conditions, and (5) to measure a response of the first contaminant sensor over time, wherein the measured response of the first contaminant sensor is a thermodynamic response which varies with mass of one or more contaminants to which the system has been exposed in the environment over time and which are deposited on the first interface structure of the first contaminant sensor.

19. A system, comprising:

electronic circuitry comprising a control system;

a primary combustible gas sensor in electrical connection with the electronic circuitry to determine if an analyte gas is present based on a response of the primary combustible gas sensor;

a trigger combustible gas sensor in electrical connection with the electronic circuitry to determine if the analyte gas is present based on a response of the trigger combustible gas sensor, wherein the electronic circuitry is configured to operate the trigger combustible gas sensor to detect a value of the response at or above a threshold value, the primary combustible gas sensor being activated from a low-power state upon the threshold value being detected by the trigger combustible gas sensor; and a first contaminant sensor in electrical connection with the electronic circuitry and being positioned separate and spaced from the primary combustible gas sensor and from the trigger combustible gas sensor, the electronic circuitry further being configured to measure a response of the first contaminant sensor over time, the measured response of the first contaminant sensor varying with an amount of one or more contaminants to which the system has been exposed in the environment over time.

20. A system for detecting an analyte gas in an environment, comprising:

a first gas sensor, a first contaminant sensor separate and spaced from the first gas sensor, a first filter pathway between the first gas sensor and the environment, the first filter pathway having a first capacity to remove at least one of one or more contaminants, a second filter pathway between the first contaminant sensor and the environment, the second filter pathway having a second capacity to remove at least one of the one or more contaminants, wherein the second capacity is less than the first capacity, and electronic circuitry in electrical connection with the first gas sensor to determine if the analyte gas is present based on a response of the first gas sensor, the electronic circuitry further being in electrical connection with the first contaminant sensor to measure a response of the first contaminant sensor over time, the measured response of the first contaminant sensor varying with an amount of the one or more contaminants to which the system has been exposed in the environment over time.

21. The system of claim 20 wherein the first capacity comprises a first adsorbent filtration capacity and the second capacity comprises a second adsorbent filtration capacity, less than the first adsorbent filtration capacity.

\* \* \* \* \*